US010203231B2

(12) United States Patent
Benson et al.

(10) Patent No.: US 10,203,231 B2
(45) Date of Patent: Feb. 12, 2019

(54) SONDE

(71) Applicant: Hach Company, Loveland, CO (US)

(72) Inventors: Tom Benson, Loveland, CO (US);
Dennis Clark, Loveland, CO (US);
Erik Host-Steen, Loveland, CO (US);
Scott David Janson, Loveland, CO
(US); Ken Labar, Loveland, CO (US)

(73) Assignee: HACH COMPANY, Loveland, CO (US)

(*) Notice: Subject to any disclaimer, the term of this patent is extended or adjusted under 35 U.S.C. 154(b) by 363 days.

(21) Appl. No.: 14/804,798

(22) Filed: Jul. 21, 2015

(65) Prior Publication Data
US 2016/0025530 A1 Jan. 28, 2016

Related U.S. Application Data

(60) Provisional application No. 62/027,943, filed on Jul. 23, 2014.

(51) Int. Cl.
G01D 18/00 (2006.01)
G01N 33/18 (2006.01)
G06N 3/02 (2006.01)

(52) U.S. Cl.
CPC ......... G01D 18/00 (2013.01); G01N 33/1886 (2013.01); G06N 3/02 (2013.01)

(58) Field of Classification Search
None
See application file for complete search history.

(56) References Cited

U.S. PATENT DOCUMENTS

| 6,021,664 | A | 2/2000 | Granato et al. |
| 2005/0009192 | A1* | 1/2005 | Page ................ C02F 1/006 436/55 |
| 2006/0016260 | A1* | 1/2006 | Smith ................ G01P 21/00 73/504.03 |
| 2008/0168339 | A1 | 7/2008 | Hudson et al. |
| 2009/0002148 | A1* | 1/2009 | Horvitz ............. G06Q 10/047 340/514 |
| 2013/0191064 | A1 | 7/2013 | Park et al. |

OTHER PUBLICATIONS

Gummadi, Ramakrishna et al., "Declarative Failure Recovery for Sensor Networks", AOSD '07, Mar. 12-16, 2007, Vancouver, Canada, 12 pages, ACM Digital Library.

(Continued)

Primary Examiner — Charles Garber
Assistant Examiner — Alia Sabur
(74) Attorney, Agent, or Firm — Ference & Associates LLC

(57) ABSTRACT

An apparatus can include a controller; memory accessible to the controller; a bus operatively coupled to the controller; sensor circuitry operatively coupled to the bus where the sensor circuitry generates measurement information representative of an environmental condition; and where the controller determines codes, each of the codes representative of an individual operational state of the apparatus, and where the controller associates, in the memory, at least a portion of the measurement information with at least one of the codes.

20 Claims, 26 Drawing Sheets

(56) References Cited

OTHER PUBLICATIONS

Szewczyk, Robert et al., "Lessons from a Sensor Network Expedition", EWSN 2004, LNCS 2920, 16 pages, Springer-Verlag Berlin Heidelberg.
Ramanathan, Nithya et al., "Designing Wireless Sensor Networks as a Shared Resource for Sustainable Development", 2006, 10 pages, IEEE Digital Library.
Ramanathan, Nithya et al., "Rapid Deployment with Confidence: Calibration and Fault Detection in Environmental Sensor Networks", UCLA Technical Reports, 2006, 16 pages, University of California.
Gaura, Elena et al., "Wireless Sensor Networks: Deployments and Design Frameworks", Book, ISBN No. 9781441958334 (Print), ISBN No. 9781441958341 (Electronic), 290 pages (Abstract Attached—3 pages), 2010, Springer, New York.
European Patent Office, Supplementary European Search Report, dated Feb. 2, 2018, 3 pages, European Patent Office.

* cited by examiner

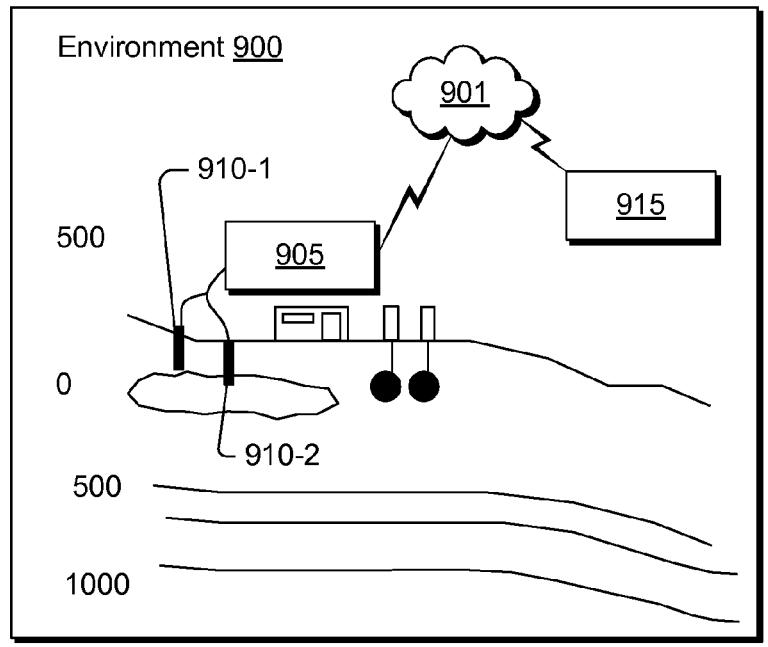
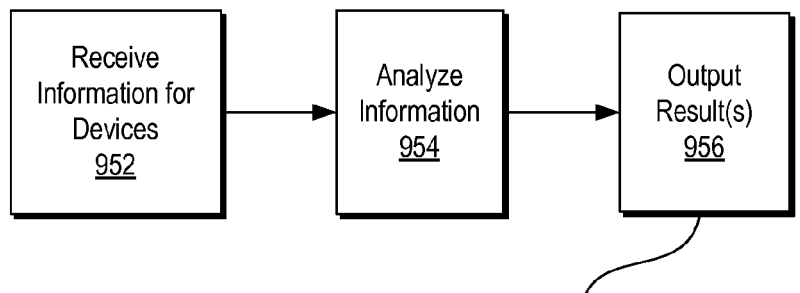
Fig. 9

| Data Structure 1502 |
|---|
| Device Diagnostic Code (time t) 1503 |
| Device Code and UI Revision 1504 |
| Device DOB (Master Time) 1505 |
| Other 1506 |

Example Information 1510

| Device Status | Status Bit Definition |
|---|---|
| Device Family | Real-World Measurement(s) |
| Device Model | Device Family Implementation |
|  |  |
| Device Code and UI Revision | Device Code Revision and UI Revision |
| Device DOM | Device Date of Mfg. |
| Device Serial No. | Device Serial No. |

Fig. 15

Example Information 1610

- X  Temperature
- X  Circulator
- X  Conductivity
-    DO
- X  LDO
- X  pH
- X  ORP
- X  Depth 10 meter
- X  Depth 25 meter
-    Depth 100 meter
-    Depth 200 meter
- X  Total Dissolved Gas
- X  Turbidity
- X  Chlorophyll a
-    Rhodamine WT
-    Blue-Green Algae Fresh
-    Blue-Green Algae Marine
- X  Chlorine
- X  Ammonium/Ammonia
- X  Nitrate
- X  Chloride
- X  Barometric Pressure
- X  Central Wiper
- X  DO/Conductivity
- X  pH/ORP
- X  Temperature/Circulator
- X  Com Module –USB
-    Com Module –USB / SDI-12
-    Com Module –USB / RS232 Modbus
-    Com Module –USB / RS485 Modbus
-    Com Module –USB / RS232 TTY
- X  Master X
-    Sonde Y
- X  Sonde Z
- X  Battery –Alkaline
- X  Virtual –external parameter source

Fig. 16

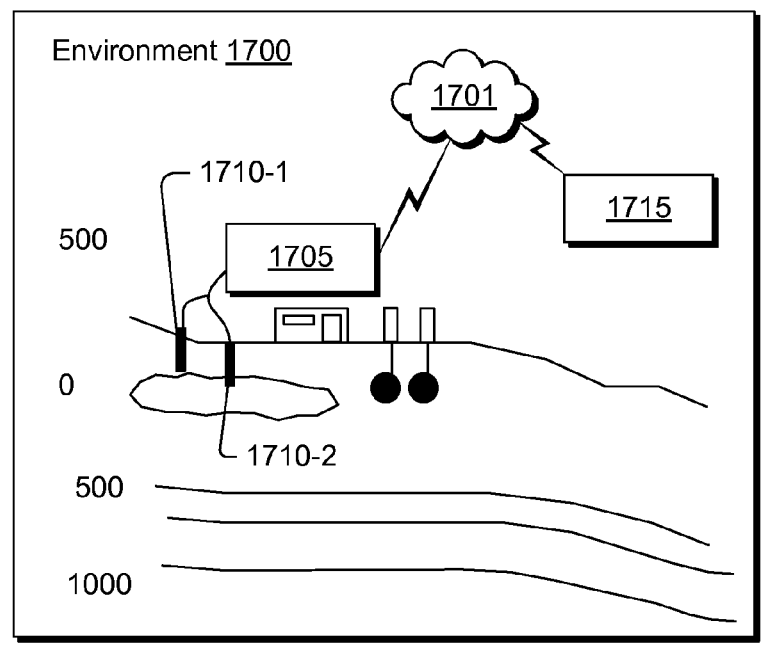
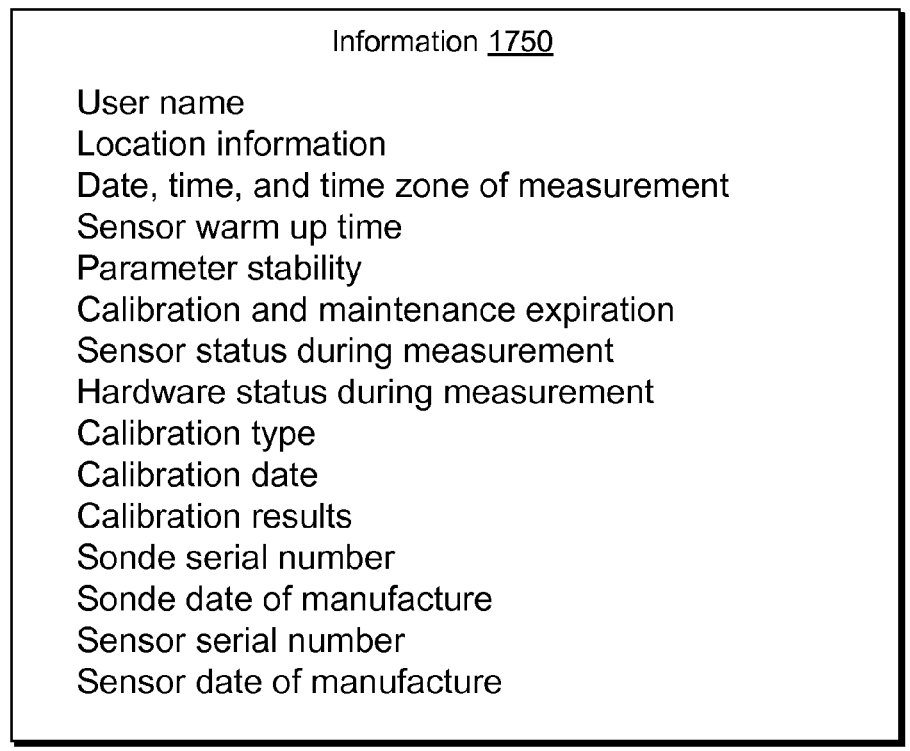
Fig. 17

SONDE

RELATED APPLICATIONS

This application claims priority to and the benefit of a U.S. Patent Application having Ser. No. 62/027,943, filed 23 Jul. 2014, which is incorporated by reference herein.

BACKGROUND

A sonde or probe can include one or more sensors and associated circuitry to monitor water-related attributes. For example, a sonde may include sensors to monitor temperature, conductivity, salinity, dissolved oxygen, pH, turbidity, and depth. A sonde may include memory that can store information, an interface for transmission of information, etc. An analysis of information acquired by a sonde may indicate status of an environment (e.g., an aqueous environment, etc.).

BRIEF DESCRIPTION OF THE DRAWINGS

Features and advantages of the described implementations can be more readily understood by reference to the following description taken in conjunction with the accompanying drawings.

FIG. 9 is a series of diagrams including an example of an environment and an example of a method.

FIG. 15 is a series of diagrams of an example of a data structure and examples of information.

FIG. 16 is a diagram of a data structure that includes example information.

FIG. 17 is a series of diagrams of an example of an environment that includes equipment and an example of information as may be associated with equipment.

DETAILED DESCRIPTION

The following description includes the best mode presently contemplated for practicing the described implementations. This description is not to be taken in a limiting sense, but rather is made merely for the purpose of describing general principles of the implementations. The scope of the described implementations should be ascertained with reference to the issued claims.

Figure 1:
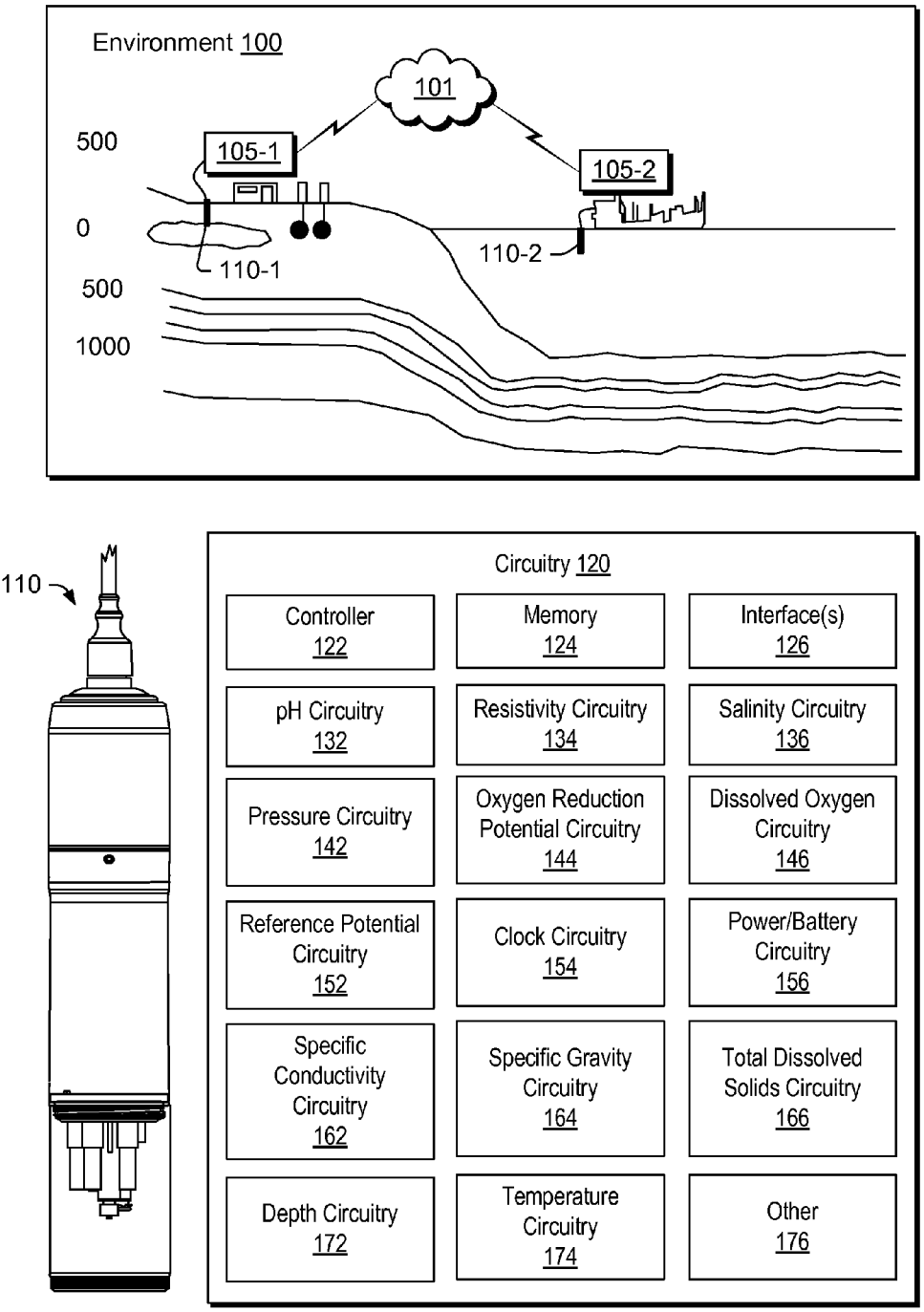
FIG. 1 is a series of diagrams including an example of an environment and examples of equipment.

FIG. 1 shows an example of an environment 100 that includes equipment that may be implemented for monitoring the environment 100. As shown, the equipment can include a network 101, electronic equipment 105-1 and 105-2 that can be operatively coupled to the network 101 and sondes 110-1 and 110-2 that can be operatively coupled to the electronic equipment 105-1 and 105-2. As an example, one or more of the sondes 110-1 and 110-2 may include an interface or interfaces that can operatively couple to electronic equipment (e.g., the electronic equipment 105-1 and 105-2), a network (e.g., the network 101), etc.

In the example of FIG. 1, the sonde 110-1 is implemented to monitor land-based conditions while the sonde 110-2 is implemented to monitor sea-based conditions. As an example, a land-based implementation may monitor for leakage from a tank, a pipe, a river, a stream, a lake, etc.

Environmental monitoring may involve processes and activities that aim to characterize and/or monitor quality of an environment. Environmental monitoring may occur prior to, during or after preparation of an environmental impact assessment. Environmental monitoring may be implemented to establish a current status of an environment or to establish a trend in one or more environmental parameters. Results of monitoring may be reviewed, analyzed statistically and reported. A monitoring program may consider use of data prior to monitoring. Monitoring may be subject to rules, regulations, etc.

FIG. 1 shows an example of a sonde 110, which may include one or more types circuitry 120. As an example, the sonde 110 can include a controller 122, memory 124 and one or more interfaces 126. In such an example, the controller 122 may be a microcontroller (e.g., ARM, ARC, etc.) that may be powered by a power source (e.g., battery, power cable, etc.). Such a controller may interact with other circuitry such as one or more of pH circuitry 132, resistivity circuitry 134, salinity circuitry 136, pressure circuitry 142, oxygen reduction potential (ORP) circuitry 144, dissolved oxygen (DO) circuitry 146, reference potential (RP) circuitry 152, clock circuitry 154, power/battery circuitry 156, specific conductivity (SC) circuitry 162, specific gravity (SG) circuitry 164, total dissolved solids (TDS) circuitry 166, depth circuitry 172, temperature circuitry 174 and other circuitry 176.

A sonde such as, for example, the sonde 110, may provide measured values that may describe characteristics of an environment. Information associated with measured values can provide context that may help in assessing an environment, operation of a sonde, performance of a sonde, quality of data, etc. Contextual information may be referred to, with respect to measured data, as, for example, metadata (e.g., data about the measured data). As an example, contextual information may be quantitative and/or qualitative.

Contextual information may prove useful, at times, in helping to notice problems, judge data quality, ascertain comparability between datasets, and build trustworthiness in measurement results. For example, contextual information may assist with answering questions about hydrology, ecology, etc.

As an example, a sonde may store and/or generate contextual information. As an example, a sonde may be inspected, for example, personally on-site (e.g., via visual or other inspection) and/or using on-site equipment (e.g., a remote camera, a drone, etc.). Such inspection may generate contextual information.

As an example, a sonde may store contextual information (e.g., metadata) in association with measured values. In such an example, metadata can exist for measured data (e.g., measured values). Some examples of contextual information include user name that generated data, location information about where the data were collected, date, time, and time zone of when the data were collected, sonde settings like sensor warm up time used during the measurement, whether the sensors were stable during measurement, whether sensor calibration and maintenance are expired, sensor and sonde status during the measurement. As an example, a sonde may store contextual information as part of a file such as, for example, a log file.

After acquiring measurements, a user may question whether the measurements or results derived therefrom are useable, for example, because of poor accuracy, spatial and temporal orientation, or relevance to a question under consideration. As an example, where information about measurement acquisition, functional state of an instrument during measurement, creator of the data, and time, date, and location of data creation are available, uncertainty about one or more measurements may be reduced (e.g., and misleading conclusions avoided). With an increase in data quality via contextual information, various benefits may be realized (e.g., confidence in reporting, confidence in field operations, etc.).

As an example, contextual information may help generate answers regarding sensor and system performance over time, timeliness and effectiveness of calibration and maintenance procedures, and repair and replacement plan efficiency. As an example, contextual information may be analyzed to determine an operational state of circuitry of a sensor, circuitry of a sonde, etc. As an example, an operational state may be represented as a code (e.g., or codes). For example, operational states may be codified and a particular state represented by a code or codes (e.g., consider a code per sensor, etc.). As an example, a code may be information as to one or more aspects of measurement information, for example, as to whether a measured values is acceptable for inclusion in an environmental assessment (e.g., optionally with respect to one or more statistics, rules, regulations, etc.).

Figure 2:
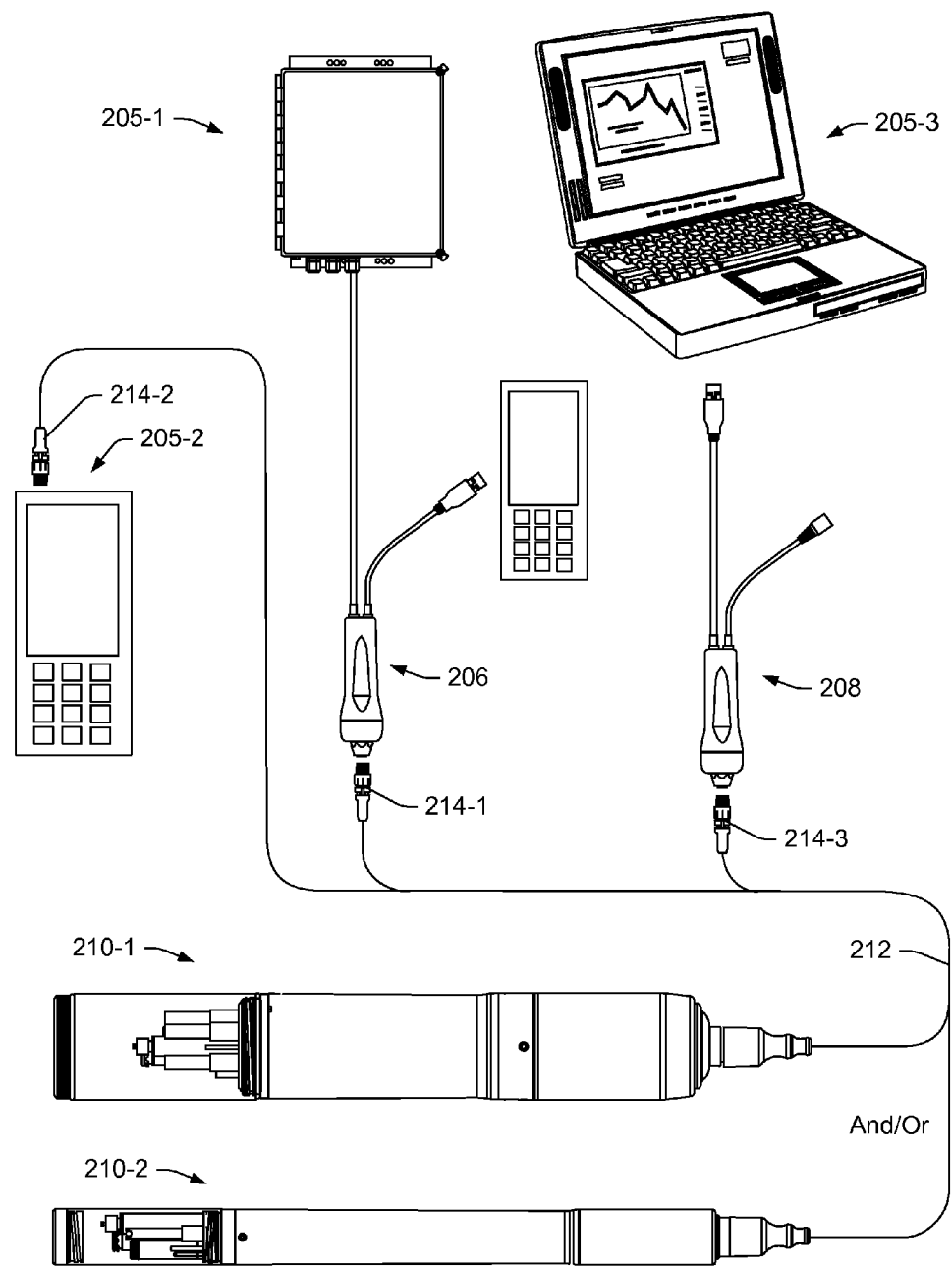
FIG. 2 is a series of diagrams of examples of equipment.

FIG. 2 shows examples of equipment 205-1, 205-2, 205-3, 206, 208, 212, 214-1, 214-2, 214-3 that may be implemented in one or more systems that include one or more sondes 210-1 and 210-2. The equipment 205-1, 205-2 and 205-3 may be operatively coupled to a sonde or sondes for receiving information, transmitting information, transmitting power, receiving power, etc. (e.g., via one or more interfaces). As an example, the equipment 205-1 can include a processor and memory, the equipment 205-2 can include a processor and memory and the equipment 205-3 can include a processor and memory.

Figure 3:
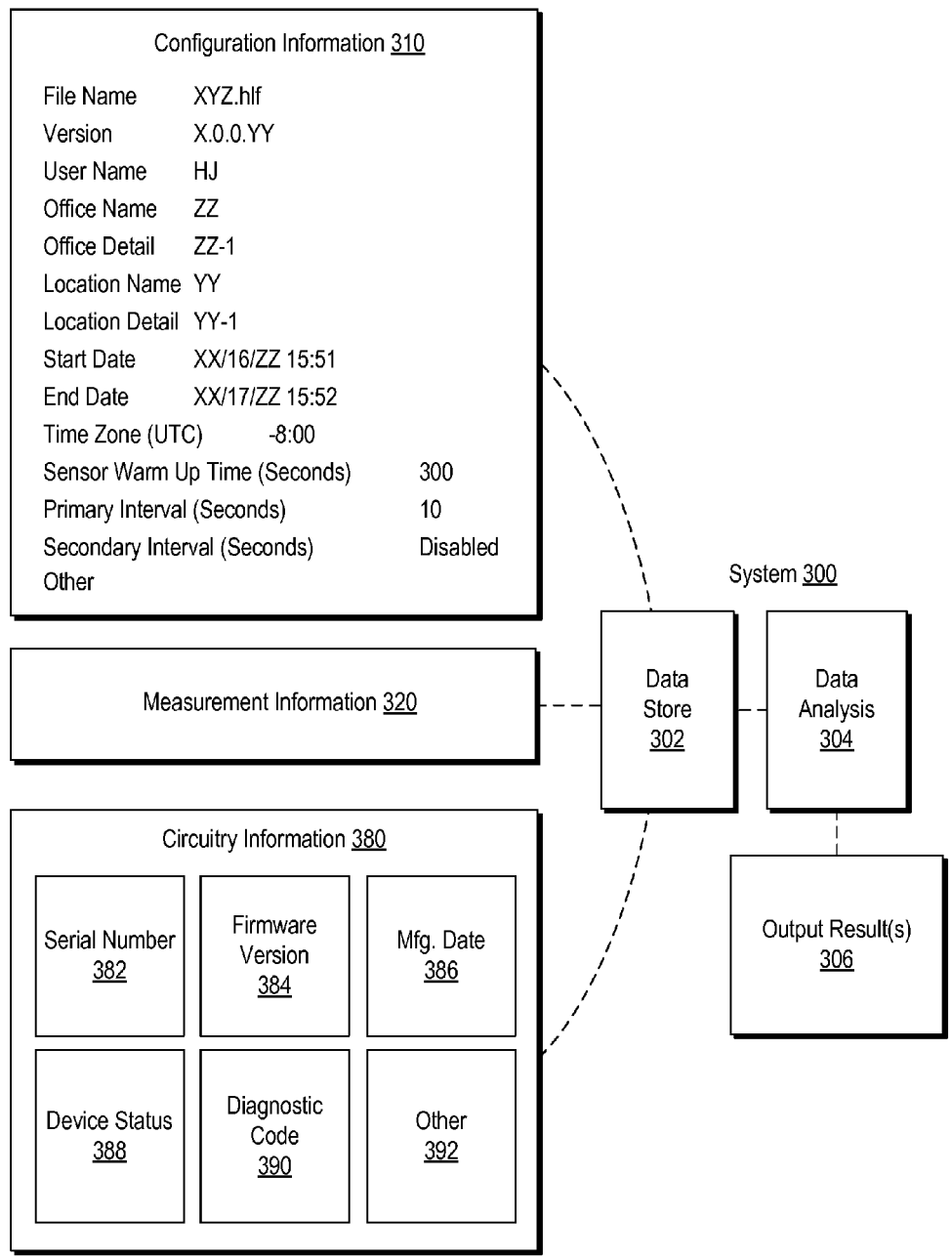
FIG. 3 is a diagram of an example of a system.

FIG. 3 shows a block diagram of an example of a system 300 that includes a data store block 302, a data analysis block 304 and an output block 306, for example, for output of information such as a result or results based at least in part on an analysis of data.

As shown in the example of FIG. 3, data may include information such as configuration information 310, measurement information 320 and circuitry information 380. The configuration information 310 may include equipment generated information and/or human input information. The measurement information 320 can include measurements that represent one or more environmental conditions (e.g., values as to one or more environmental parameters). The circuitry information 380 may include information such as serial number 382, firmware version 384, manufacture data 386, device status 388 (e.g., of a circuitry device, component, etc.), one or more diagnostic codes 390 and/or other information 392.

As an example, the data analysis block 304 may be implemented in circuitry as part of a sonde (e.g., via a controller and controller-executable instructions, etc.). As an example, the data analysis block 304 may be implemented in circuitry as part of a computing device (e.g., via a processor and processor-executable instructions, etc.). As an example, the data analysis block 304 may be implemented in circuitry as part of local equipment and/or as part of remote equipment.

As an example, configuration information may include entered information (e.g., user input) and/or may include generated information (e.g., system generated information). For example, GPS circuitry may determine a location (e.g., coordinates) of a sonde and/or a user may input location of a sonde. As an example, a sonde may include clock circuitry that can generate time information (e.g., time stamps, etc.). As an example, one or more events, interactions, etc. may be stamped with a time stamp according to clock circuitry of a sonde. As an example, a sonde may include circuitry that can update clock circuitry via wireless communication with broadcasting equipment.

Figure 4:
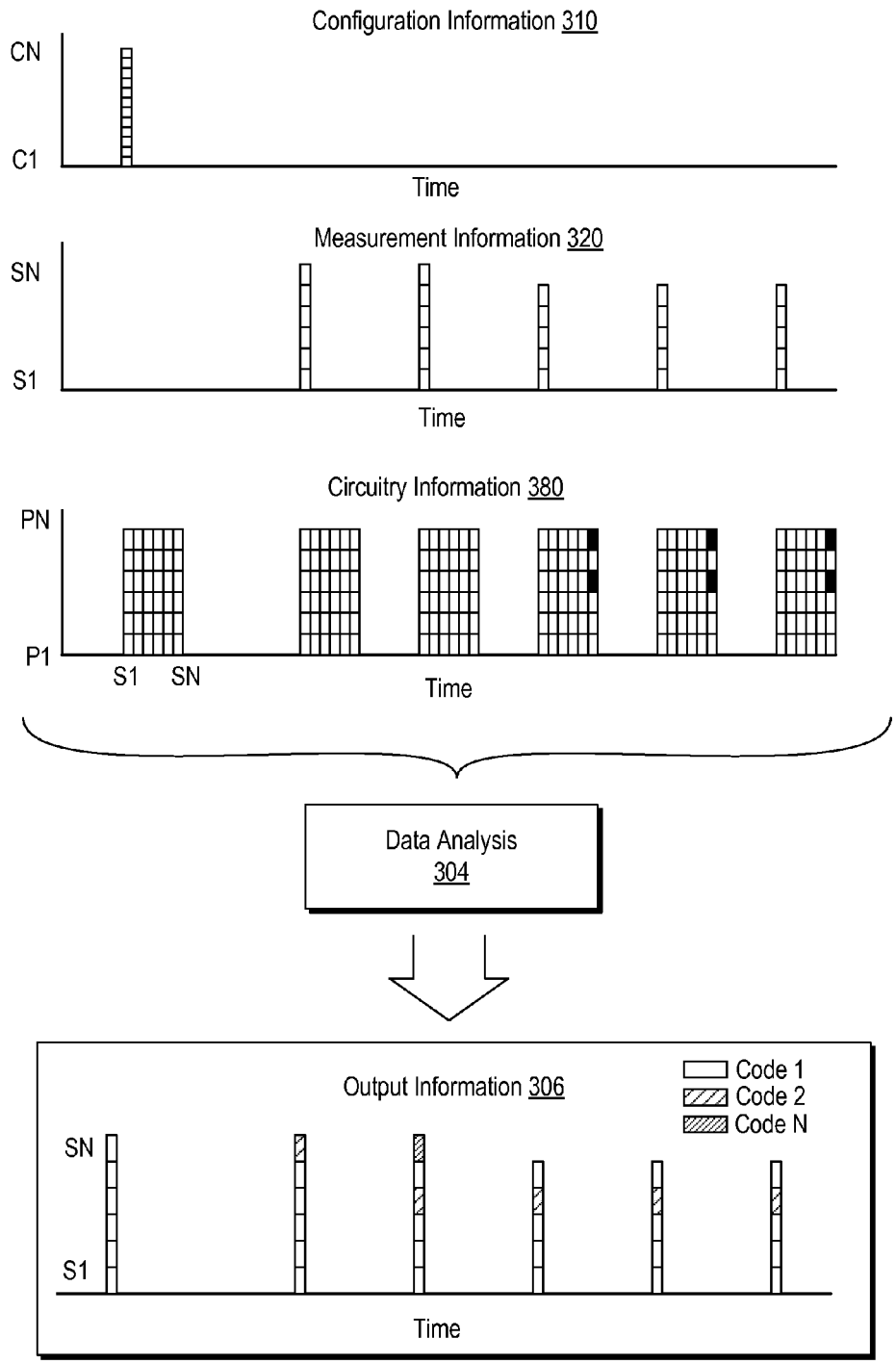
FIG. 4 is a diagram of an example of an information analysis.

FIG. 4 shows an example scenario where the configuration information 310 includes configuration parameters C1 to CN with values at an initial time, where the measurement information 320 includes measurement parameters S1 to SN with values at various times (e.g., time intervals), and where the circuitry information 380 includes circuitry parameters P1 to PN with values at various times (e.g., time intervals) for corresponding individual measurement parameters S1 to SN (e.g., consider arrays of circuitry parameter values).

In FIG. 4, the data analysis block 304 may analyze at least a portion of the information to generate the output information 306 (e.g., as one or more results). For example, the output information 306 may be structured as output parameters for S1 to SN at various times. Such output parameters may be in the form of one or more codes (e.g., Code 1, Code 2, . . . , Code N). Such codes may be informative as to status of equipment, status of a sonde or sondes, etc. Such codes may be indicative of how equipment, a sonde, etc. was configured, oriented, etc. As an example, a code may be information as to one or more aspects of measurement information, for example, as to whether a measured values is acceptable for inclusion in an environmental assessment (e.g., optionally with respect to one or more statistics, rules, regulations, etc.).

As an example, a code may be a warning status code, which may indicate a level of concern. For example, consider a code that indicates that circuitry is to be powered down as soon as possible to avoid possible damage to such circuitry. Other code examples may include battery replacement, cleaning of one or more sensor windows, inspection for leakage, repacking one or more seals with grease, replacing one or more components, reorienting a sensor (e.g., a sonde), etc.

Figure 5:
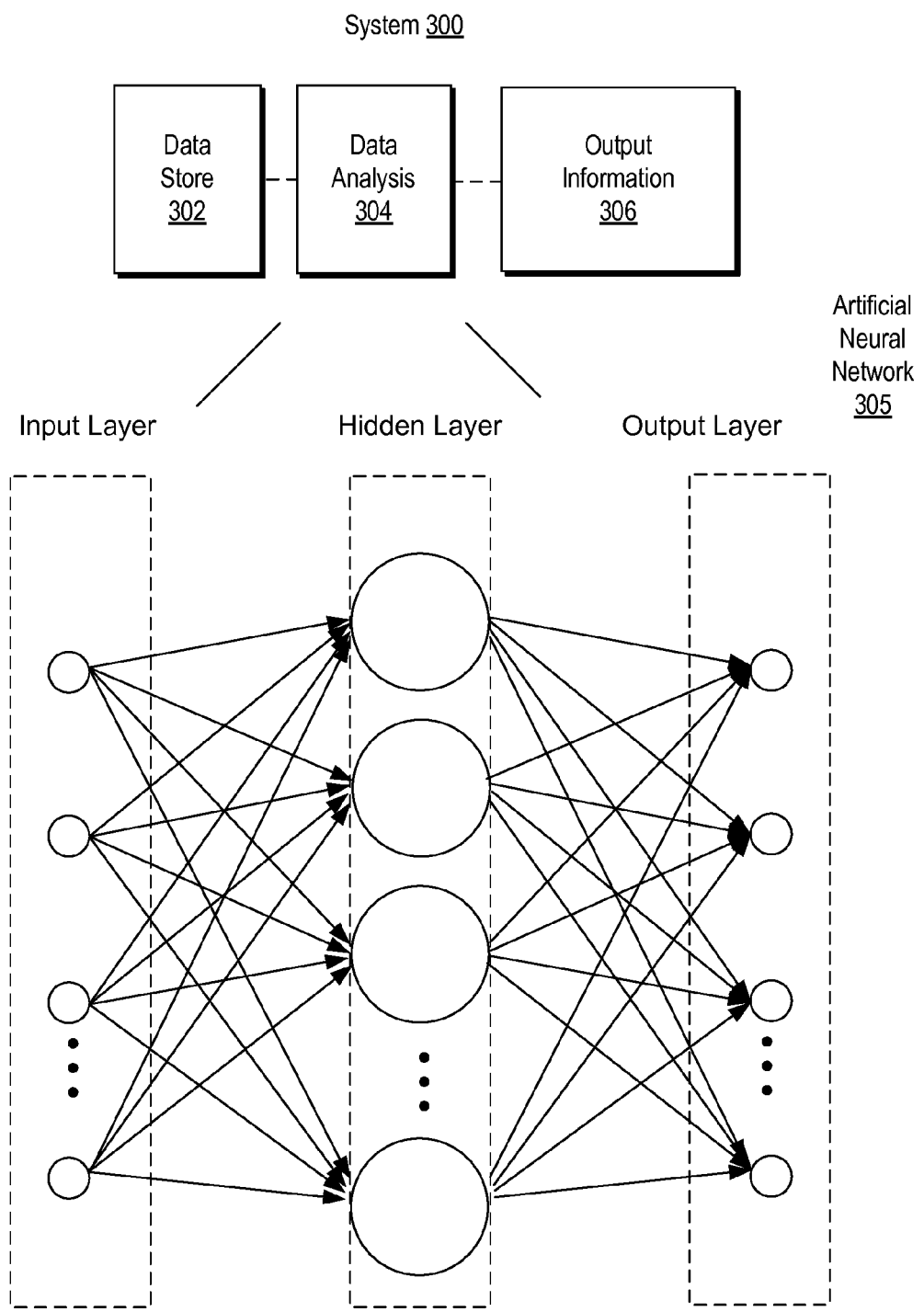
FIG. 5 is a diagram of an example of the system of FIG. 3 that includes one or more artificial neural networks.

FIG. 5 shows the system 300 where the data analysis block 304 may include or be based at least in part on a technique 305. In the example of FIG. 5, the technique 305 illustrated is an artificial neural network (ANN) that includes at least one input layer, at least one hidden layer and at least one output layer.

ANNs find use in recognition scenarios such as handwriting recognition for determination of individual characters, and for speech recognition for determination of individual sounds and words, etc. In the example of FIG. 5, the technique 305 can recognize statuses based on input, which may include one or more of the configuration information 310, the measurement information 320 and the circuitry information 380. As an example, the technique 305 can involve training, for example, using actual information and/or synthetic information.

For example, the technique 305 may be defined by a set of input neurons which may be activated by receipt of information. After being weighted and transformed by a function or functions (e.g., as may be determined via historical analyses, training, etc.), the "activations" of these neurons are then passed on to other neurons. Such a process may be repeated until finally, an output neuron is "activated". The output neuron can correspond to a status, which may optionally be represented as a code.

As an example, one or more algorithms may be defined based at least in part on inputs and outputs of an ANN. For example, consider an algorithm that includes variables where values for the variables may be associated with outputs. Such an approach may optionally operate via a look-up such as in a look-up table (LUT). As an example, a LUT approach may be implemented using memory and a controller that can execute instructions.

As an example, a predictive model may be generated based at least in part on historical information. A predictive model may be generated using predictive analytics, for example, consider use of one or more statistical techniques in combination with machine learning and data mining. As an example, a method may include building a predictive model using historical information and then using the predictive model to make predictions about future, or otherwise unknown, events, states, etc. (e.g., based on current information and/or historical information).

As an example, training of a predictive model may be on-going, for example, based at least in part on acquisition of data, whether quantitative and/or qualitative. Such data may be via field operations, laboratory testing, manufacturer information, etc. As an example, a predictive model may be trained using measured values from sensors of a sonde or sondes and using contextual information as may be associated with one or more sondes.

As an example, a predictive model may be, in part, a virtual machine of a device such as a sonde. For example, characteristics of a sonde may be modeled in software (e.g., a software emulation of a sonde). In such an example, time may be accelerated such that the virtual machine performs various actions that can establish states, which may be possible states of a real machine (e.g., a sonde). Where a possible state is uncovered that may be problematic, a method can include taking one or more corrective actions. For example, a signal may be transmitted to a sonde to adjust one or more settings, update firmware, etc. As an example, an alert may be transmitted to a device, an account, etc., for example, consider an email alert, a text alert, etc. Such an alert may include a link (e.g., URL) to instructions associated with the alert (e.g., retrieve sonde, check X, replace Z, etc.).

As an example, a sonde may include one or more security mechanisms such as an encryption mechanism that can encrypt information. A sonde may store at least a portion of information in memory of the sonde in an encrypted form. For example, certain information (e.g., configuration information, circuitry information, codes, etc.) may be reserved for manufacturer use. As an example, a method can include transmitting encrypted information to a remote location and de-encrypting the information and analyzing the de-encrypted information.

As an example, a code-based system may reduce transmission bandwidth. For example, a sonde that is configured to generate codes (e.g., via a controller and firmware, etc.), may transmit codes via a communication technique such as text messaging. For example, where a sonde includes or is operatively coupled to cellular circuitry, the sonde may transmit a SMS to a cellular number. In such an example, a sonde may be programmed to respond to receipt of one or more codes transmitted via SMS, etc. For example, a sonde may parse a SMS for a code and then change its operational state based at least in part on the code (e.g., by changing one or more settings, etc.).

As an example, a sonde may include memory, a controller and executable instructions stored in the memory to cause the sonde to analyze inputs and determine one or more outputs. In such an example, the inputs may include information such as one or more of configuration information, measurement information and circuitry information and the outputs may include codes.

As an example, the artificial neural network 305 of FIG. 5 may be implemented in the system 300 to output predictions based at least in part on input information. For example, consider a method that includes performing a calibration on a sensor of sonde where results of the calibration are input to the system 300. As an example, an output may be information that indicates that the calibration results do not sufficiently match expected calibration results. Such output may indicate a failed calibration and/or that one or more circuits are not performing as expected. In such an example, one or more recommended courses of action may be output and optionally taken for remedial action, etc.

Figure 6:
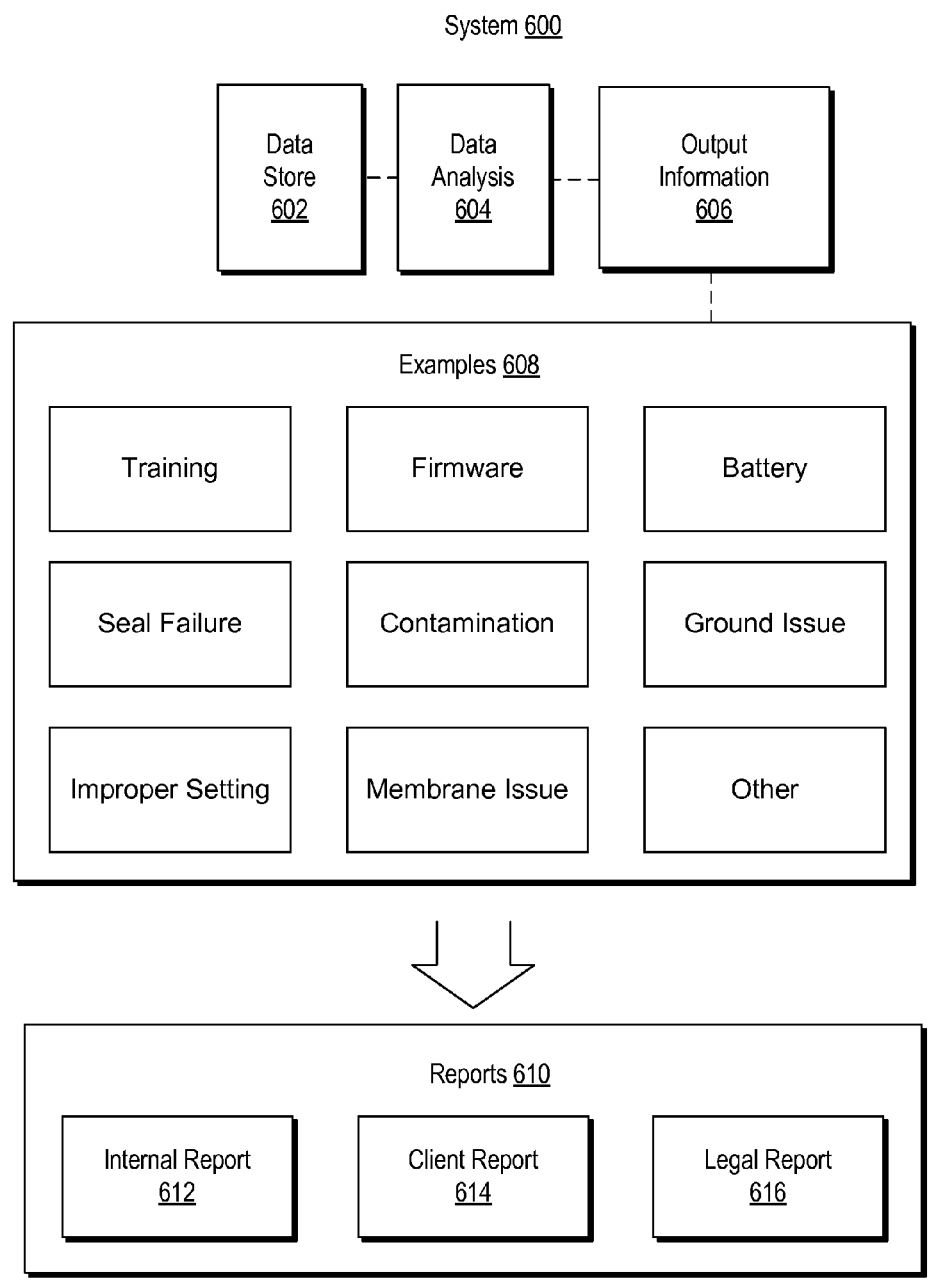
FIG. 6 is a diagram of an example of a system.

FIG. 6 shows an example of a system 600 that includes a data store block 602, a data analysis block 604 and an output block 606. Examples of output information 608 can include information related to training, firmware, power supply (e.g., battery, etc.), seal failure, contamination, ground issues, improper setting(s), membrane(s), and/or one or more other types of information.

As an example, one or more reports 610 may be generated such as an internal report 612, a client report 614 and/or a legal report 616. As an example, a legal report may be formatted and optionally communication to one or more regulatory entities, clients, etc. As an example, one or more quality related issues may be identified in a report.

Figure 7:
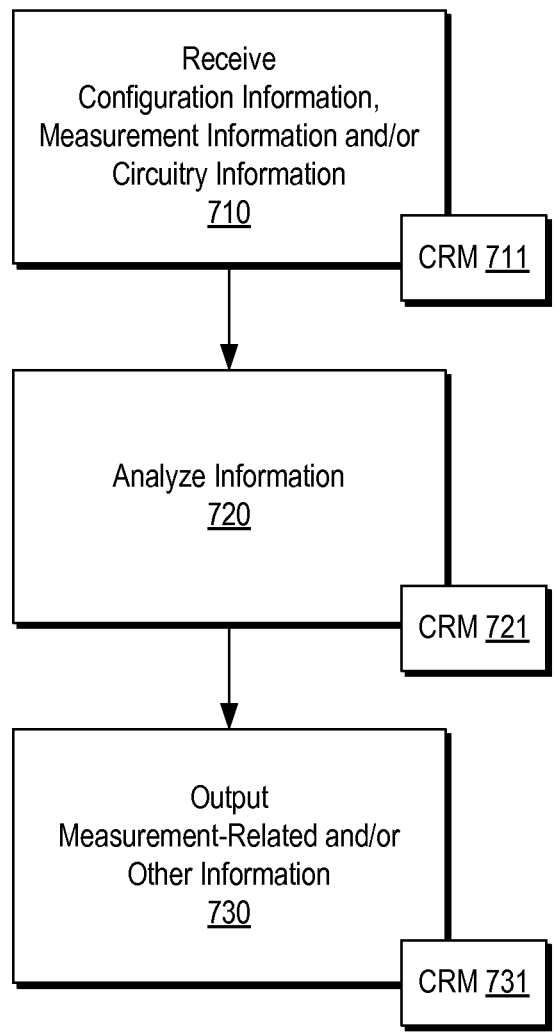
FIG. 7 is a diagram of an example of a method.

FIG. 7 shows an example of a method 700 that includes a reception block 710 for receiving configuration information, measurement information and/or circuitry information, an analysis block 720 for analyzing at least a portion of received information and an output block 730 for outputting measurement-related and/or other information, optionally as one or more codes, reports, etc.

In the example of FIG. 7, the blocks 710, 720 and 730 are shown with computer-readable media (CRM) blocks 711, 721 and 731. A CRM block may include instructions executable by a controller, a processor, etc. to cause a device, a system, etc. to perform one or more actions such as one or more of the actions of the method 700.

Figure 8:
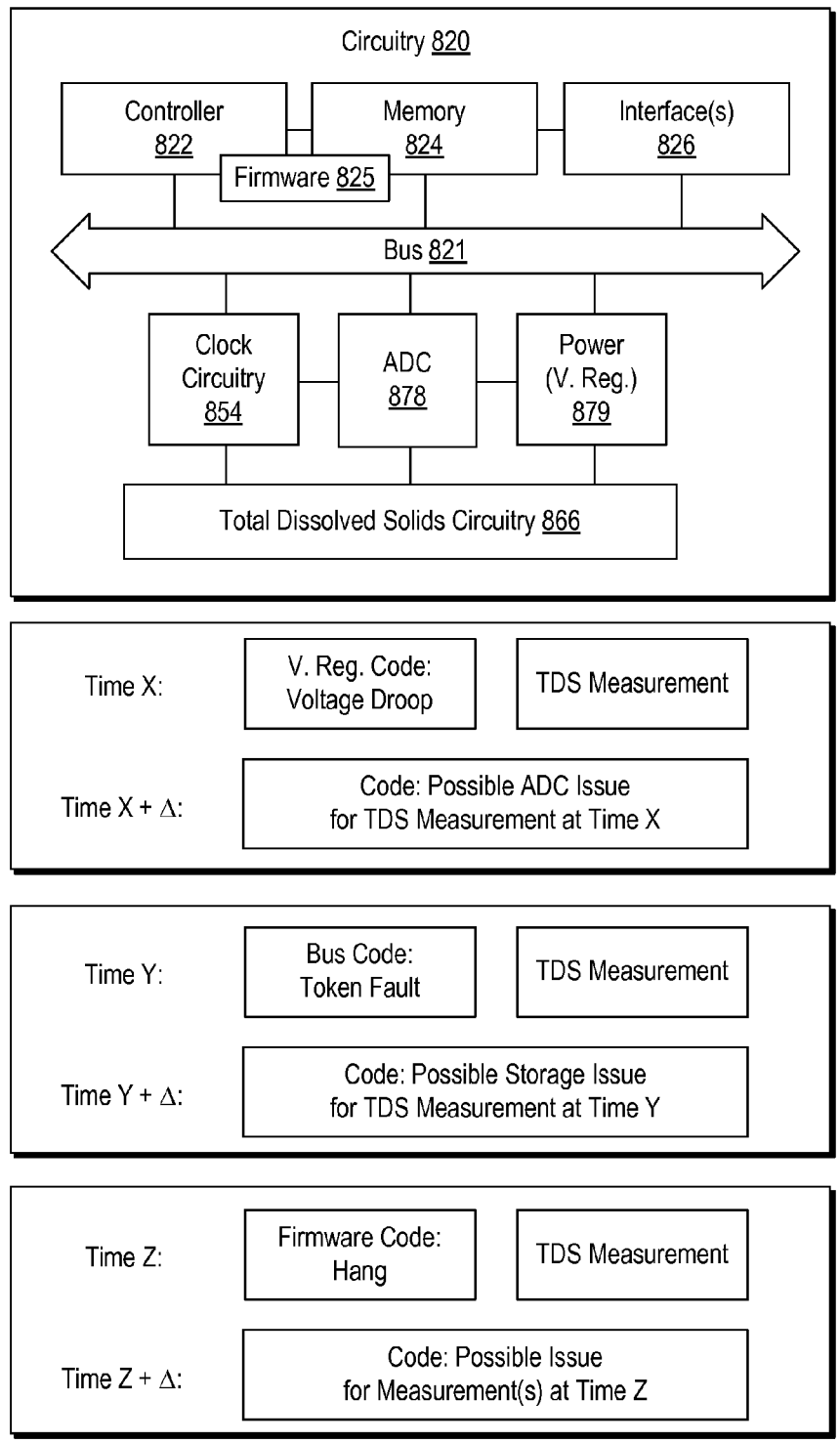
FIG. 8 is a diagram of an example of circuitry and examples of scenarios.

FIG. 8 shows an example of circuitry 820 that includes a bus 821, a controller 822, memory 824, firmware 825, one or more interfaces 826, clock circuitry 854, an analog-to-digital converter (ADC) 878, a power supply 879 and total dissolved solids (TDS) circuitry 866. As an example, the circuitry 820 may be at least in part in a device such as a sonde.

FIG. 8 shows three example scenarios for a time X, a time Y and a time Z. The time X scenario shows a power supply code indicative of a voltage droop at the time of a TDS measurement. As the power supply may power an ADC, a code may be generated and stored in memory, transmitted, etc. where the code is associated with the TDS measurement (e.g., in a table or other data structure or data structures).

The time Y scenario shows a bus code indicative of token fault at the time of a TDS measurement. As the bus may carry the measurement from the TDS circuitry for storage in memory, a code may be generated and stored in memory, transmitted, etc. where the code is associated with the TDS measurement (e.g., in a table or other data structure or data structures).

The time Z scenario shows a firmware code indicative of hang (e.g., controller hang) at the time of a TDS measurement. As the controller may operate according to the firmware to process the measurement from the TDS circuitry, a code may be generated and stored in memory, transmitted, etc. where the code is associated with the TDS measurement (e.g., in a table or other data structure or data structures).

FIG. 9 shows an example of an environment 900 that includes a network 901, equipment 905, sensor devices 910-1 and 910-2 and remote equipment 915. FIG. 9 also shows a method 950 that includes a reception block 952 for receiving information for devices, an analysis block 954 for analyzing information and an output block 956 for outputting information. Various examples of types of output information are shown in the example of FIG. 9, including: Sensor 910-1 Performance/Sensor 910-2 Performance, Orientation Report, Measurements Report, Timeliness of Calibrations Report, Effectiveness of Calibration Report, Maintenance Procedure Plan, Repair Recommendation Plan, Replacement Recommendation Plan, Etc.

Figure 10:
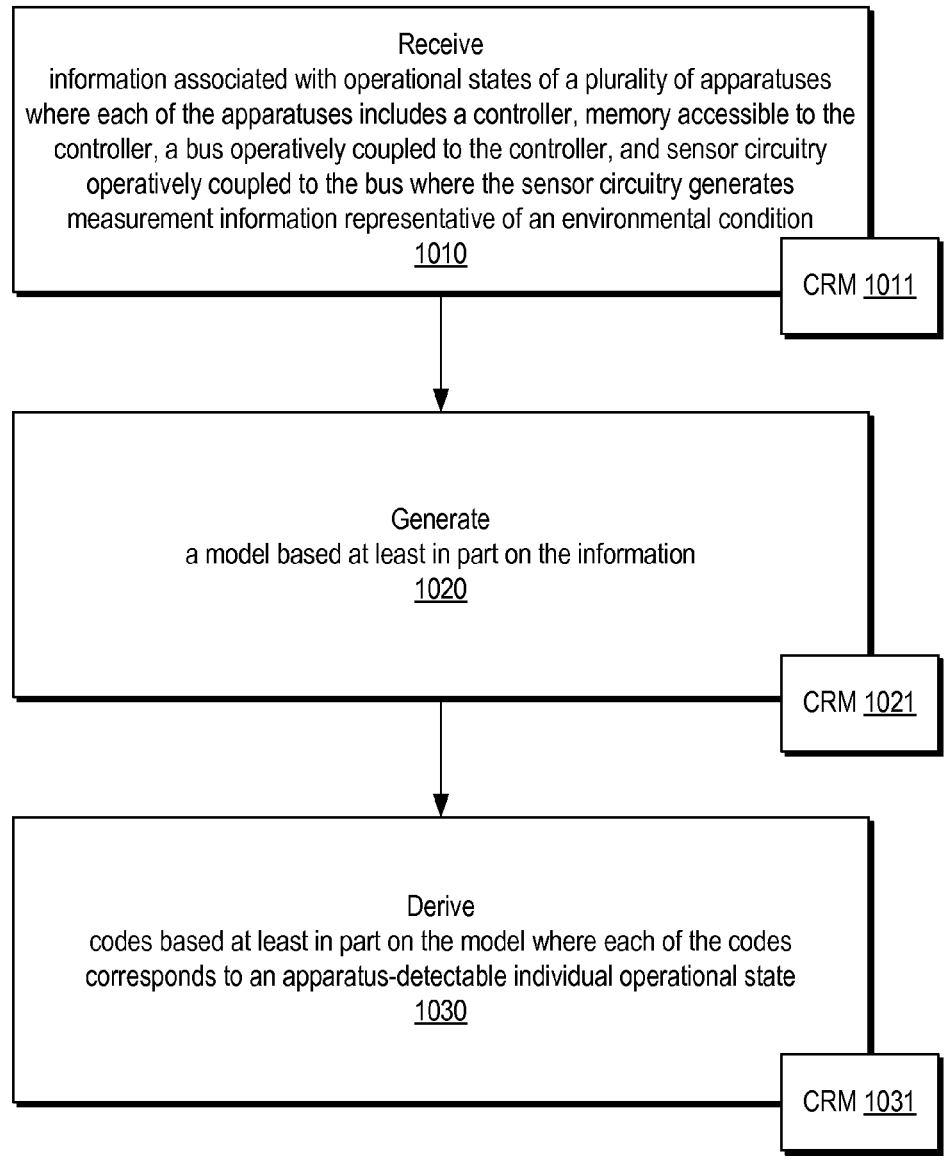
FIG. 10 is a diagram of an example of a method.

FIG. 10 shows an example of a method 1000 that includes a reception block 1010 for receiving information associated with operational states of a plurality of apparatuses where each of the apparatuses includes a controller, memory accessible to the controller, a bus operatively coupled to the controller, and sensor circuitry operatively coupled to the bus where the sensor circuitry generates measurement information representative of an environmental condition; a generation block 1020 for generating a model based at least in part on the information; and a derivation block 1030 for deriving codes based at least in part on the model where each of the codes corresponds to an apparatus-detectable individual operational state. In such an example, the model can include an artificial neural network. As an example, the generation block 1020 may include generating a model by training an artificial neural network to generate a trained artificial neural network (e.g., as a model).

As an example, the reception block 1010 of the method 1000 can include receiving sets of configuration information corresponding to the individual apparatuses. In such an example, each of the sets of configuration information may include configuration information generated by the individual apparatuses. As an example, sets of configuration information may include configuration information input to individual apparatuses. As an example, received information can include sets of circuitry information corresponding to the individual apparatuses (e.g., consider static information such as manufacture information, dynamic information such as dynamic status information, etc.).

In the example of FIG. 10, the blocks 1010, 1020 and 1030 are shown with computer-readable media (CRM) blocks 1011, 1021 and 1031. A CRM block may include instructions executable by a controller, a processor, etc. to cause a device, a system, etc. to perform one or more actions such as one or more of the actions of the method 1000.

Figure 11:
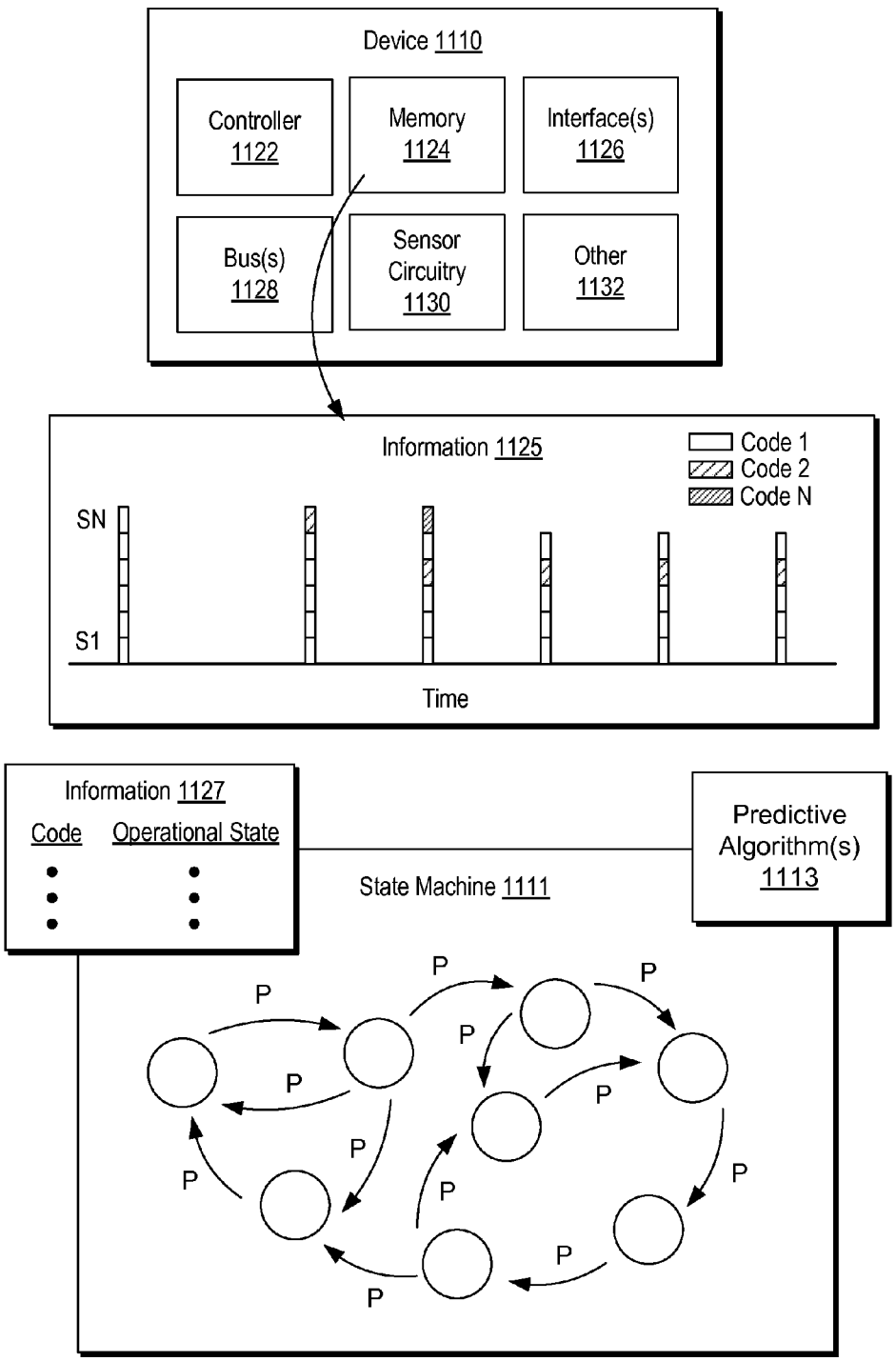
FIG. 11 is a series of diagrams of an example of a device, examples of information, an example of a state machine and an example of one or more predictive algorithms.

FIG. 11 shows an example of a device 1100 that includes a controller 1122; memory 1124 accessible to the controller 1122; a bus 1128 operatively coupled to the controller 1122; sensor circuitry 1130 operatively coupled to the bus 1128 where the sensor circuitry 1130 generates measurement information representative of an environmental condition; and where the controller 1122 determines codes, each of the codes representative of an individual operational state of the device, and where the controller 1122 associates, in the memory 1124, at least a portion of the measurement information with at least one of the codes.

As an example, codes may include codes derived from an analysis of historical individual operational states. As an example, one or more codes may correspond to an individual operational state such as a bus error, a calibration error of sensor circuitry, a controller instruction error, an analog-to-digital conversion error, a memory error, a reset error, a clock error, etc.

FIG. 11 also shows information 1125, which may be information stored in the memory 1124 of the device 1110. As an example, information 1127 may be available locally and/or remotely to associated a code with an operational state. As an example, the device 1110 may be modeled, at least in part, as a state machine 1111. In such an example, the state machine 1111 can include individual states where transitions may occur, optionally with associated probabilities. As an example, one or more predictive algorithms 1113 may be available to, given a particular state, predict a future state. As an example, consider receiving one or more codes associated with a device, translating the one or more codes to an operational state and then using a state machine and predictive algorithm to predict a future state, which may be a likely future state of the device. Depending on the nature of the future state, a method may include generating an alert, taking corrective action or actions, etc.

Figure 12:
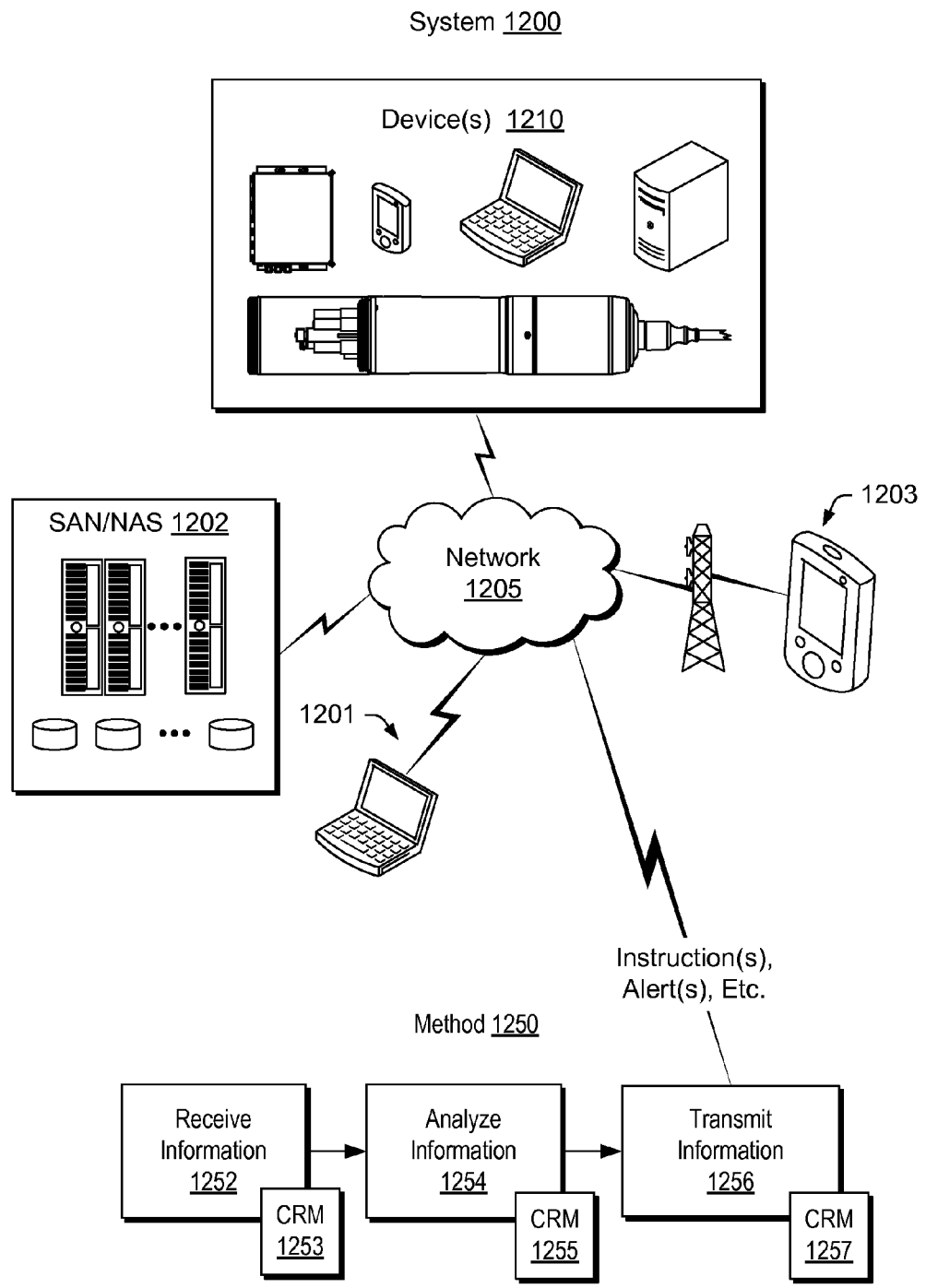
FIG. 12 is a series of diagrams of an example of a system and an example of a method.

FIG. 12 shows an example of a system 1200 that includes a device 1201, storage equipment 1202, a device 1203, a network 1205 and a device 1210, which may be a sensor device or a device operatively coupled to a sensor device. As an example, the device 1210 may include features of the device 1110 of FIG. 11.

FIG. 12 also shows an example of a method 1250 that includes a reception block 1252 for receiving measurement information and associated codes from a device that includes a controller that includes memory accessible to the controller, a bus operatively coupled to the controller, sensor circuitry operatively coupled to the bus where the sensor circuitry generates measurement information representative of an environmental condition, where the controller determines the codes, each of the codes representative of an individual operational state of the device; an analysis block 1254 for analyzing the received measurement information and associated codes; and a transmission block 1256 for transmitting at least one instruction to the device based at least in part on the analyzing. In such an example, analyzing can include inputting at least a portion of the received codes into a model where the model may include or be a predictive model. In such an example, the method 1250 can include predicting a mode of failure (e.g., of the device) via the predictive model and, for example, transmitting at least one instruction that may be a corrective instruction intended to avoid the predicted mode of failure (e.g., of the device when implemented).

In the example of FIG. 12, the blocks 1252, 1254 and 1256 are shown with computer-readable media (CRM) blocks 1253, 1255 and 1257. A CRM block may include instructions executable by a controller, a processor, etc. to cause a device, a system, etc. to perform one or more actions such as one or more of the actions of the method 1250. As an example, a server may include memory as a CRM that includes instructions such as instructions of one or more of the blocks 1253, 1255 and 1257.

As an example, the system 1200 can include one or more communication networks, one or more remote servers (e.g., with associated processor or processors, memory, instructions, network interfaces, etc.), processor-executable instructions for predictive processing, processor-executable instructions for generating alerts, and circuitry for issuing alerts, for example, to notify one or more individuals of imminent maintenance or problems, etc.

Figure 13:
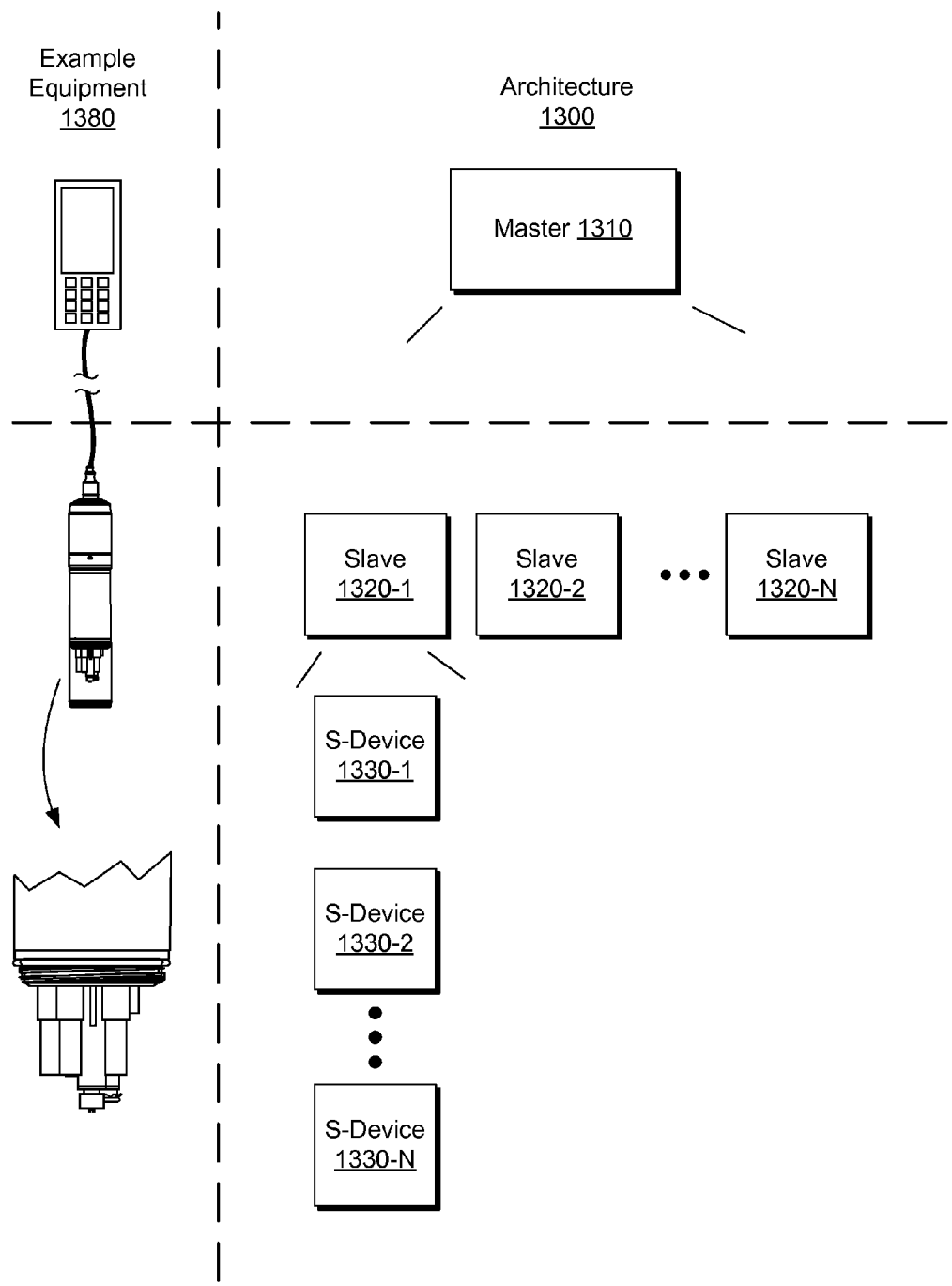
FIG. 13 is a series of diagrams of an example of an architecture and examples of equipment.

FIG. 13 shows an example of an architecture 1300 that includes a master level with master equipment 1310, a slave level with slave equipment 1320-1, 1320-2, . . . 1320-N, and a slave device level with slave device equipment 1330-1, 1330-2, . . . , 1330-N. Some examples of equipment 1380 are also shown in FIG. 13. For example, consider equipment as in FIG. 1 or FIG. 2.

As an example, a model or models may include representative equations, parameters, variables, etc. for one or more entities in an architecture such as the architecture 1300 of FIG. 13. As an example, a model may include one or more artificial neural networks that may be trained (e.g., via machine learning). As an example, a model may receive one or more inputs and generate one or more outputs where such one or more outputs may represent one or more likely states (e.g., operational states of a system).

As an example, master equipment may include a computer that is instructed by circuitry (e.g., circuits, firmware, software, etc.). As an example, slave equipment may be a probe (e.g., a sonde) that can perform various tasks such as, for example, tasks associated with sensing. As an example, a slave device may be a sensor or device included in, attached to, etc. a piece of slave equipment. As an example, a slave device may include an identity. As an example, a slave device may include circuitry that allows the slave device to identify itself, to be addressed, etc. (e.g., for communication, etc.). As a sonde may be slave equipment that includes a plurality of slave devices, for example, where one or more of the slave devices may be configurable and, for example, optionally addressable via a respective address (e.g., identity, etc.).

As an example, an architecture may include a component level that includes one or more components. As an example, a component may be a subsystem of a slave device. For example, consider a sonde as slave equipment that includes a slave device such as, for example, a pH sensor where the pH sensor includes a secondary ORP option as an associated subsystem component. As an example, a communications module as a slave device may also include more than one component. For example, consider a communication module that includes communication circuitry and one or more of GPS circuitry, a barometric pressure sensor, etc.

As an example, an architecture may include one or more protocols for transmission of information. For example, master equipment may implement a protocol that can address slave equipment, slave devices and optionally components, for example, for transmission of information. Such information may include call information, configuration information, etc. As an example, where an entity operates using executable code (e.g., software, firmware, etc.), such executable code and/or instructions that can instruct such executable code may be transmitted.

As an example, a slave device may be configured to initiate a transmission. For example, consider a slave device configured to initiate transmission of information to an entity in an architecture that may be at an equal level, at a lower level, at a higher level, etc.

As an example, an architecture may specify equipment features such as a clock or clocks, features to handle deployment logging, file system features, aggregation features (e.g., for parameters, data, etc.), schedule features (e.g., for services and activities to be run), system sleep/wake features, communication features, etc.

As an example, a slave device may include features to take sensor measurements, perform functions, perform activities, provide parameters reflecting sensor measurements and/or activity status, provide calibration procedures and/or records (e.g., for a sensor or sensors), execute services, execute setups, implement functionality, execute diagnostics (e.g., for its hardware), handle application downloads, implement application(s), etc.

As an example, equipment may include status information, for example, that can be offered to indicate one or more statuses. For example, consider one or more of: 0 Success, 1 Failure, 2 Wait, 3 Invalid Command Query, 4 Invalid Data Query, 5 Device Not Available, 6 Component Not Available, 7 Parameter Not Available, 8 Service Not Available, 9 Scheduled Services Not Available, 10 Log Not Available, 11 File Not Available, 12 CRC Error, 13 Buffer overrun, 14 Setup Not Available, 15 Improper Access Rights, 16 Device Error, 17 Data Not Ready, 18 Bus Timeout, 19 Duplicate Log name, 20 Log media failure, 21 Log media, bad format/unformatted, etc.

As an example, equipment may include status information, for example, that can be offered to indicate one or more statuses. For example, consider one or more of: 0 Parameter Reading Unstable, 1 Dependency Default Warning, 2 Parameter Default Warning, 3 Calibration Warning, 4 Maintenance Warning, 5 Range Error, 6 Hardware Fault, 7 Hardware Error, etc.

As an example, a slave device may be configured to perform one or more calculations. As an example, such a slave device may receive a parameter from another device/component for use in calculating a parameter value. For example, consider a slave device configured to measure fluid conductivity based at least in part on fluid temperature (e.g., conductivity dependent upon temperature or, otherwise stated, temperature is a dependency for conductivity). In such an example, if a temperature sensor is not installed then a temperature parameter may be an external dependency where a value is received from an external source. As an example, where a slave device establishes existence of an external dependency, it may set a parameter value for use (e.g., an estimated temperature) and/or issue a signal as to the existence of the external dependency (e.g., to search for a source of temperature information).

An example, a slave device may include a DO sensor. Where such a device includes circuitry to calculate a percent saturation parameter value, it may do so based at least in part on barometric pressure. As an example, user configuration information may include an external dependency that is set to be the average reading for the location the sensor is being used (e.g., to achieve desired results). As an example, a parameter may be tagged (e.g., by a status bit) when it is using a default dependency to calculate one or more parameters.

As an example, various commands may be available that can be communicated at a level, across levels, etc. of an architecture. As an example, one or more commands may be associated with logs such as a log of a slave device. As an example, a set of device commands may be available to address individual slave devices attached to or included in a slave. For example, such commands may include commands to deal with activities of a slave device; such as sensor setups, services, calibrations, maintenance and diagnostics. As an example, such commands may be issued by a master, for example, to configure and/or to identify (e.g., discover, etc.) a slave, a slave device, etc. As an example, configuration information may be include generated and/or user input information. As an example, time stamps may be generated (e.g., via one or more clocks) and stored with configuration information, discovery information, etc.

As an example, a component of a slave may be a sensor that includes sensor circuitry that can output a voltage indicative of an environmental condition. Such a voltage may be applied to an analog-to-digital converter to generate a digital value, which may be stored in memory. As an example, a calculation may be made using the digital value, optionally in conjunction with one or more other values, which may be values from the same sensor, from a different sensor, and/or from circuitry that acts to perform a function (e.g., consider a motor, a wiper, etc.). Where a calculation involves one or more values, the calculation may be classified as having dependencies. As an example, a log may store information for one or more values where the information pertains to a state of one or more components. Such information may be associated with a calculated value that represents an environmental condition. Such information may optionally be stored as a code or codes where a code may represent an operational state of an apparatus (e.g., a slave, one or more slave devices, etc.).

As an example, a method may include checking a slave (e.g., slave device, etc.) during one or more logging intervals and, for example, optionally switching a logging interval (e.g., logging interval time, trigger event for logging, etc.). For example, a sonde may be sampling twice a day, where during a sample interval an elevated turbidity is found (e.g., a check was greater than some fixed value). In such an example, the sonde (e.g., as a slave) may switch to a sampling interval of every 15 minutes to gain better resolution of measurements during the event. In such an example, if turbidity settles back down, the sample interval may return to the interval of twice a day. Such changes in interval may be stored to a log and available as information pertaining to circuitry of a slave (e.g., slave device circuitry). As an example, a method may include analyzing such log information in conjunction with other information. As an example, one or more measurements may be tagged as corresponding to an interval, an interval change, etc. As an example, one or more measurements may be stored in memory in association with a tag or tag that may be indicative of circuitry status, etc. As an example, a tag may be a code or codes where a code may represent an operational state of an apparatus (e.g., a slave, one or more slave devices, etc.).

As an example, a method may include receiving information and, based at least in part on an analysis of the information, issuing a command. For example, a command may be a slave device reset command that may aim to cause a reset of a slave device (e.g., restart, clear dependencies, clear setup, clear serial number, clear dates, etc.).

As an example, information may be in the form of a report. For example, consider a slave that may store one or more reports that pertain to the slave itself and, more particularly, to one or more slave devices included in the slave and/or attached to the slave. As an example, a report may include information such as, for example, device family, model, code revision, serial number, maintenance information, calibration information, setup information, etc.

As an example, information may include calibration information. Calibration information may include information as to timing of one or more calibrations. Such information may be used to assess measurement information. For example, a calibration may interfere with one or more other operations of a slave, one or more slave devices, etc. (e.g., duration of the calibration). As an example, calibration information may include one or more results of a calibration (e.g., values, success, failure, duration, etc.).

As an example, a calibration log may be stored in memory that may include a number of entries for calibrations. As an example, a sensor may include memory that stores a calibration log. A calibration log may include, for example, one or more of: Component Number, Calibration Number, Calibration Log Number, Calibration Diagnostic Code, Calibration Parameter, Timestamp, Calibration Interval, Operator Identifier, Operator Comment, Calibration inputs (one per calibration action), Calibration Results (e.g., raw sensor reading and/or calibrated reading and/or final calibration slope/intercept values, etc.), etc.

As an example, a command may be issued by a master, a slave, a slave device, etc. that instructs circuitry to perform one or more diagnostic processes. In such an example, one or more diagnostic results may be generated, which may be stored, communicated, etc. As an example, a diagnostic result may be a code or codes that may represent a state of circuitry, etc.

As an example, information associated with a system may include information in the form of one or more of: an Extended Diagnostics Report, a Device Calibration, a Device Calibration Result, a Device Calibration Store, a Device Service, a Device Set Serial Number, a Device Set Date of Birth, a Device Set Date of Maintenance, a Device Diagnostic, a Device Component Status, a Device Calibration Check, a Device Dependency Default Value Write, a Device Calibration Log, a Device Calibration Log Report, a Device Set Calibration Interval, etc.

As an example, a slave (e.g., a sonde, a probe, etc.) may include memory such as, for example, EEPROM. As an example, a slave may include a bus such as, for example, an I$^2$C bus. As an example, a slave may direct information via a bus to memory and direct information from memory via a bus. As an example, a slave may include a clock that can operate to generate time information, which may be, for example, timestamps for storage in memory of the slave. As an example, a slave may store location information, orientation information, etc., optionally in conjunction with time information.

As an example, an architecture may specify a log file format. For example, a log file may include a series of log entries where at least a portion of the log entries include individual timestamps. As an example, consider a log entry that includes a timestamp packet of information and optionally one or more additional packets of information. As an example, an extended log may be available, for example, to store additional information (e.g., that may be associated with a particular time, event, etc.). As an example, a log entry may be packetized with a checksum value.

Figure 14:
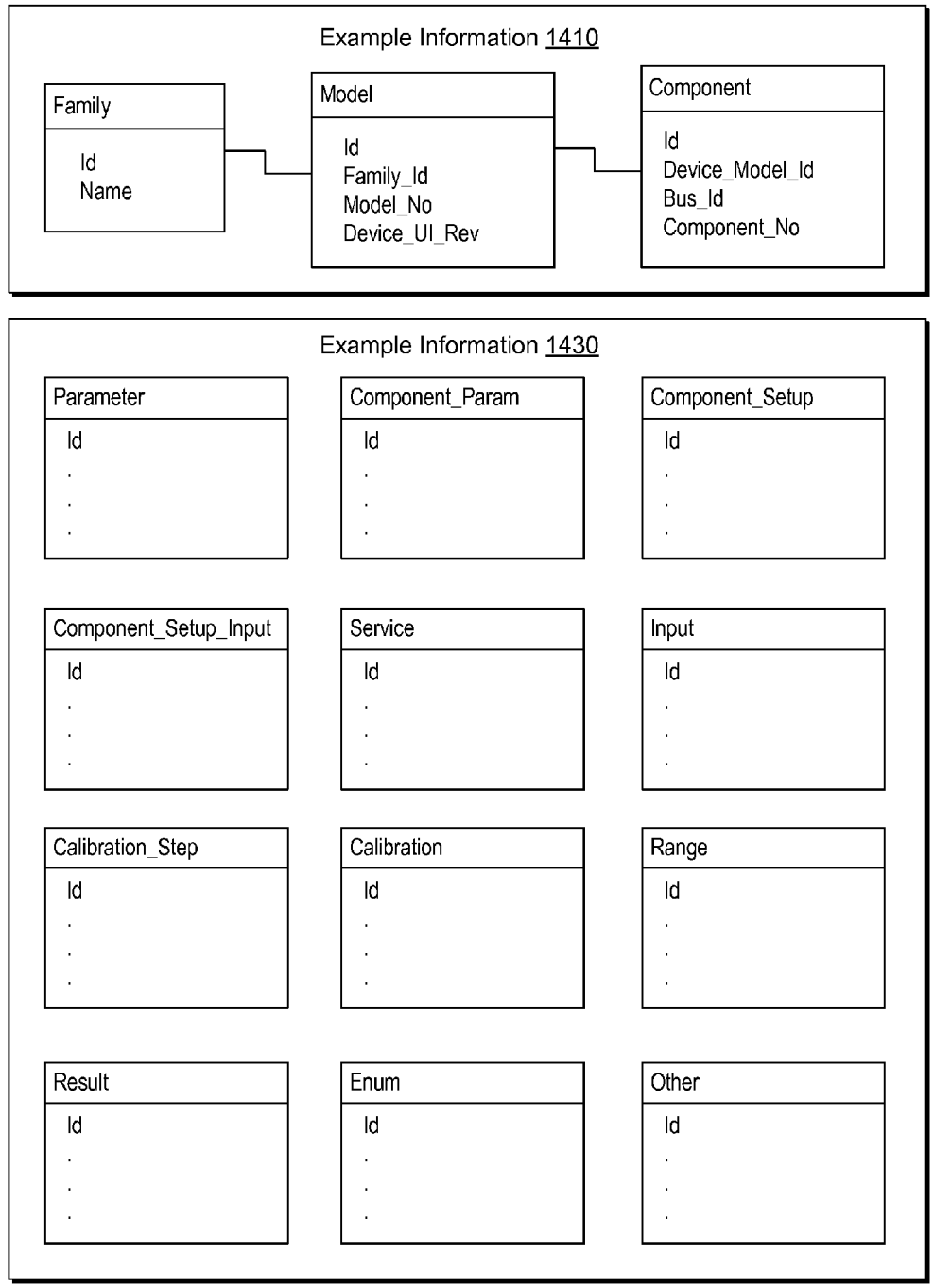
FIG. 14 is a series of diagrams of examples of information that may be stored as data structures.

FIG. 14 shows examples of information 1410 and 1430, which may be data structures, optionally linked in a database (e.g., a relational database, etc.). As an example, information can include configuration information. As an example, configuration information can include user input information, default information and/or equipment generated information (e.g., about the equipment). As an example, an input mechanism may be in the form of a graphical user interface (GUI) that allows a user to navigate fields and controls to enter information, select one or more options (e.g., default information), etc. As an example, a GUI may include features such as multi-language support, user access levels, device and component descriptions, calibration descriptions, setup descriptions, service descriptions, enumeration to text translations (e.g., for codes, etc.), etc.

As an example, a specification associated with an architecture may include one or more protocols that include levels of organization, for example, to describe parts of slave equipment. For example, consider the information 1410, which includes device family, device model, and component. In such an example, a "device-family" may group devices that report common types of data, a "device-model" may group devices that report common types of data in a common manner. For example, a device-model may have multiple components which report different data. For example, a device family for dissolved oxygen (DO) may have a deviceFamily.id=5. As an example, where two different types of DO sensors exist, each DO device can include a different model number to distinguish them in a master program.

In the example of FIG. 14, the information 1410 and 1430 may include parameters, for example, parameters that a component may return. For example, a parameter table may provide the name, abbreviation, and unit strings for individual parameter_ids. As an example, a parameter id may be calculated from loggable, raw_value, category, and number as defined by a specification. As an example, an accessConfig_enum_id may allow a programmer to restrict access to parameters used for production or service.

As an example, a component may support multiple parameters, and, as an example, each parameter may exist in more than one component. As an example, a componentParameter table may be used to combine references between two tables. For example, each componentParameter pair may include a different range for a given parameter (e.g., multiple depth sensors which each report the depth parameter, but have different depth ranges).

As an example, a setup may be used to change the way a component operates. For example, individual components may support multiple setups where, for example, each setup may include multiple inputs. As an example, a flag may be a hint to help a user application display inputs in a logical manner.

As an example, a conductivity component may include a plurality of setups. For example, consider Setup #1 that configures which temperature compensation method is used; consider Setup #2 that allows for custom temperature compensation; consider Setup #3 that enables a user to change the averaging sample count; and consider Setup #4 that allows production to set high and low gain offsets.

As an example, a setup can include one or more inputs. In such an example, the inputs can include a data type defined by a parameter dataType_enum_id. Optionally, min and max values may be set. As an example, where the dataType_enum_id='enum', then a programmer may use the 'enum' field to lookup the enum associated with this input.

As an example, a component may include one or more services, which may be user requestable. As an example, services may instruct a component to do something (e.g., perform a cleaning cycle, etc.). As an example, a plurality of flags may be associated with a service. For example, a "corrupts_readings" flag may indicate that this service will cause a component to read incorrect data while the service is running. As an example, a "scheduling_allowed" flag can indicate that a service can be scheduled for periodic execution. As another example, a "logging_allowed" flag can indicate that a service will show in the data log.

As an example, a Component-Parameter pair may include one or more calibrations. As an example, a calibration can include one or more steps (e.g., where a step includes an input). As an example, at the end of a calibration, a user (e.g., or an application) may request a calibration result, for example, to be displayed using data in a result table.

As an example, an enumeration may be an index into an enumeration array of strings, for example, that give textual description to put into a pull down or selection box of a GUI interface. Such a list may include enumeration Information in a file, in the 'enum' table. As an example, an enumeration may include a key/value pair that may be used to describe the enumeration.

As an example, consider the following enumerations: Value railed low, Value railed high, Reference voltage invalid, Parameter unable to stabilize, No value read, Watchdog Reset Error, EEPROM Error, Circulator Fault, Turbidity Motor Fault, Calibration Step Error, Device Discovery Error, bus error, TOKEN bus fault, Hardware reset occurred, Watchdog timer fault, Code software traps triggering, Main battery low, Standby Battery Low, Power on or Brown out Reset, Log media has excessive errors, Log media write error, Log storage media failure (e.g., cannot log), etc.

FIG. 15 shows an example of a data structure 1502 that includes data fields. As an example, consider a device diagnostic code field 1503, a device code and UI revision field 1504, a device date of birth (DOB) field 1505 and one or more other fields 1506.

As shown in FIG. 15, information 1510 may include device status, device family, device model, device code and UI revision, device date of manufacture (DOM), device serial number, etc. The information 1510 may be in the form of a data structure, for example, storable in memory of equipment.

FIG. 16 shows information 1610, which may be listing of components, etc. and an indication of whether such are in a device, devices, etc. For example, the information 1610 may pertain to a sonde. The information 1610 may be specified as part of an architecture such as, for example, the architecture 1300 of FIG. 13. Such information may be configuration information as associated with one or more pieces of equipment (e.g., a component, a device, etc.).

FIG. 17 shows an example of an environment 1700 that can include equipment specified according to an architecture. As an example, the environment 1700 may include a network 1701, master equipment 1705, slave equipment 1710-1 and 1710-2 and remote equipment 1715.

In FIG. 17, example information 1750 is shown, which can be associated with equipment in the environment 1700.

Examples of information can include, for example, user name that generated the data, location information about where the data were collected, date, time, and time zone of when the data were collected, sonde settings like sensor warm up time used during the measurement, whether the sensors were stable during measurement, whether sensor calibration and maintenance are expired, sensor and sonde status during the measurement. As an example, an operational state may be a stable state or an unstable state. Such states may pertain to one or more circuits such as sensor circuits (e.g., sensor circuitry).

Figure 18:
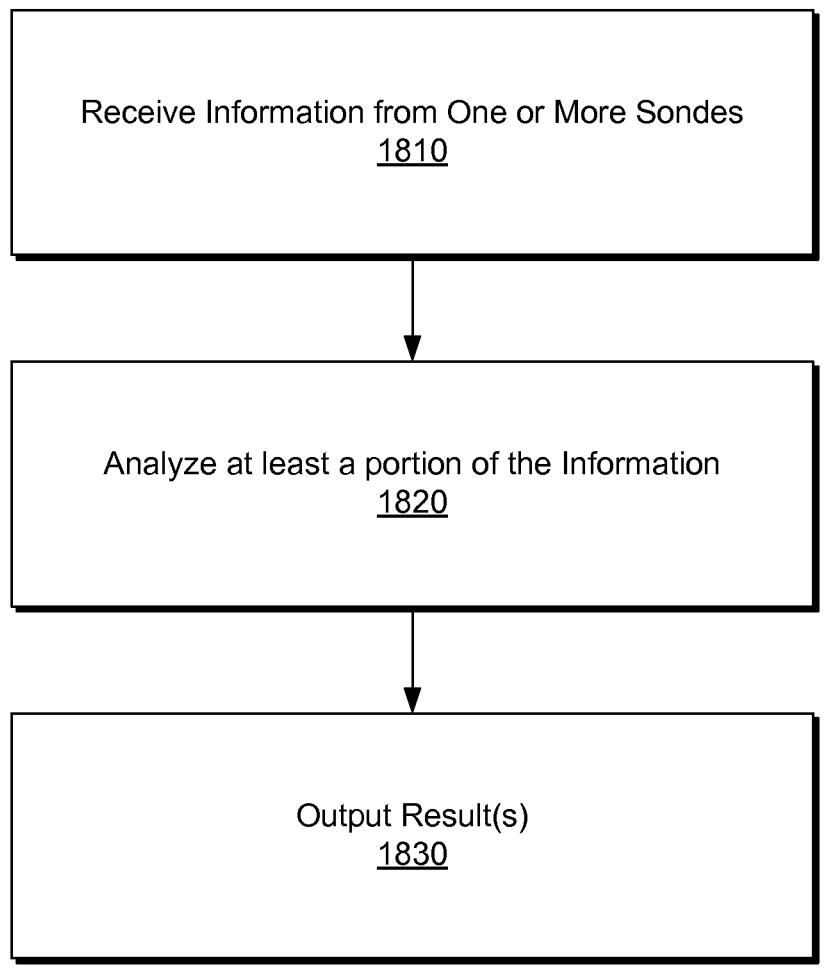
FIG. 18 is a diagram of an example of a method.

FIG. 18 shows an example of a method 1800 that includes reception block 1810 for receiving information from one or more sondes, an analysis block 1820 for analyzing at least a portion of the information and an output block 1830 for outputting at least one or more results of the analyzing.

As an example, the one or more sondes of the method 1800 may be slave equipment as specified by an architecture such as the architecture 1300 of FIG. 13. In such an example, master equipment may be configured to receive information and to analyze information.

Figure 19:
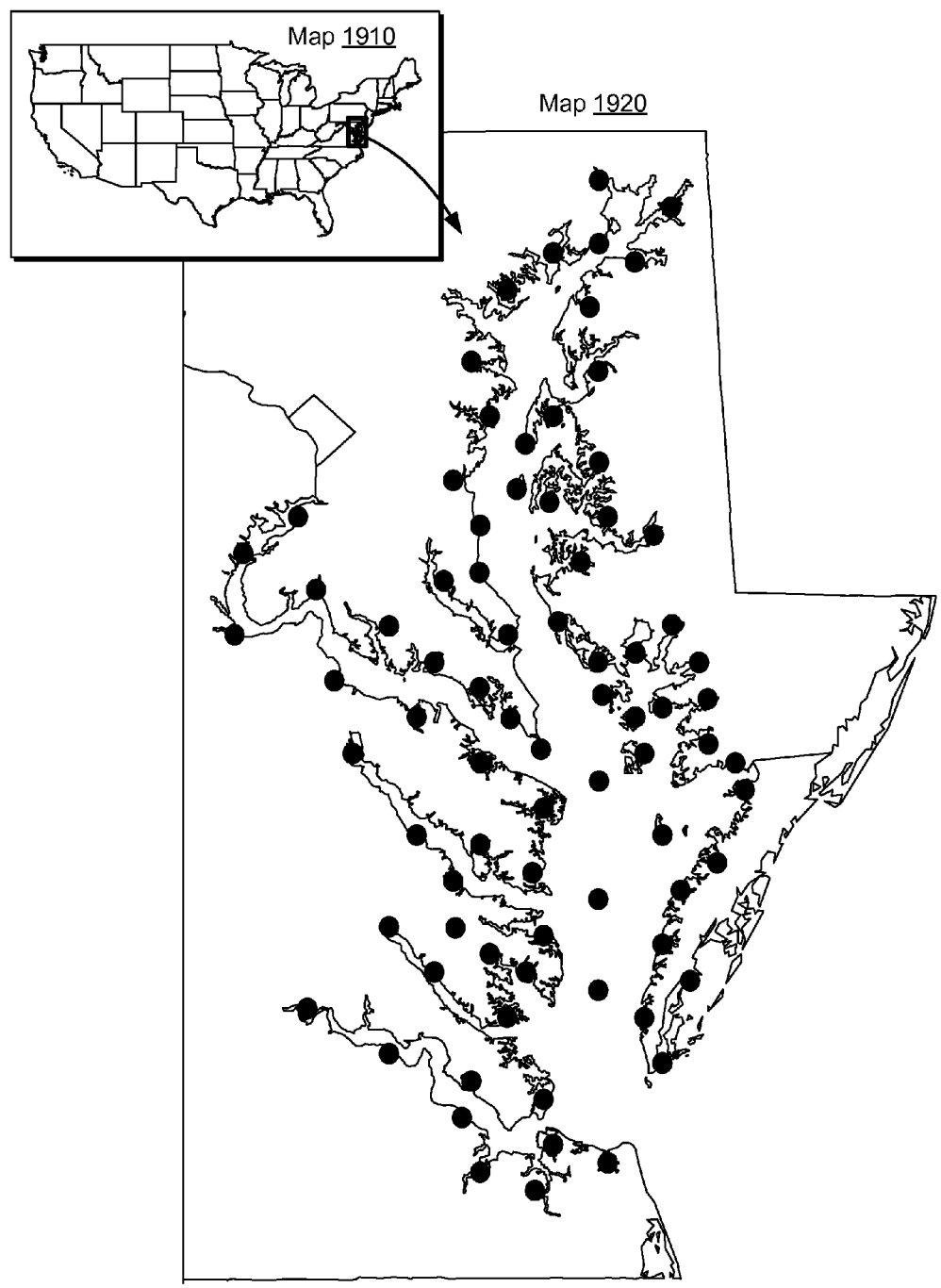
FIG. 19 is a diagram of an example of an environment that includes a plurality of sites.

FIG. 19 shows example maps 1910 and 1920 of an environment that includes a plurality of sites. The map 1920 shows the Chesapeake Bay as including tens of sites where each site can include one or more sondes. As an example, a graphical user interface (GUI) may render such a map and allow for interactions therewith. Such interactions may, for example, allow for assessment of environmental conditions and/or equipment-related conditions (e.g., sonde conditions).

Figure 20:
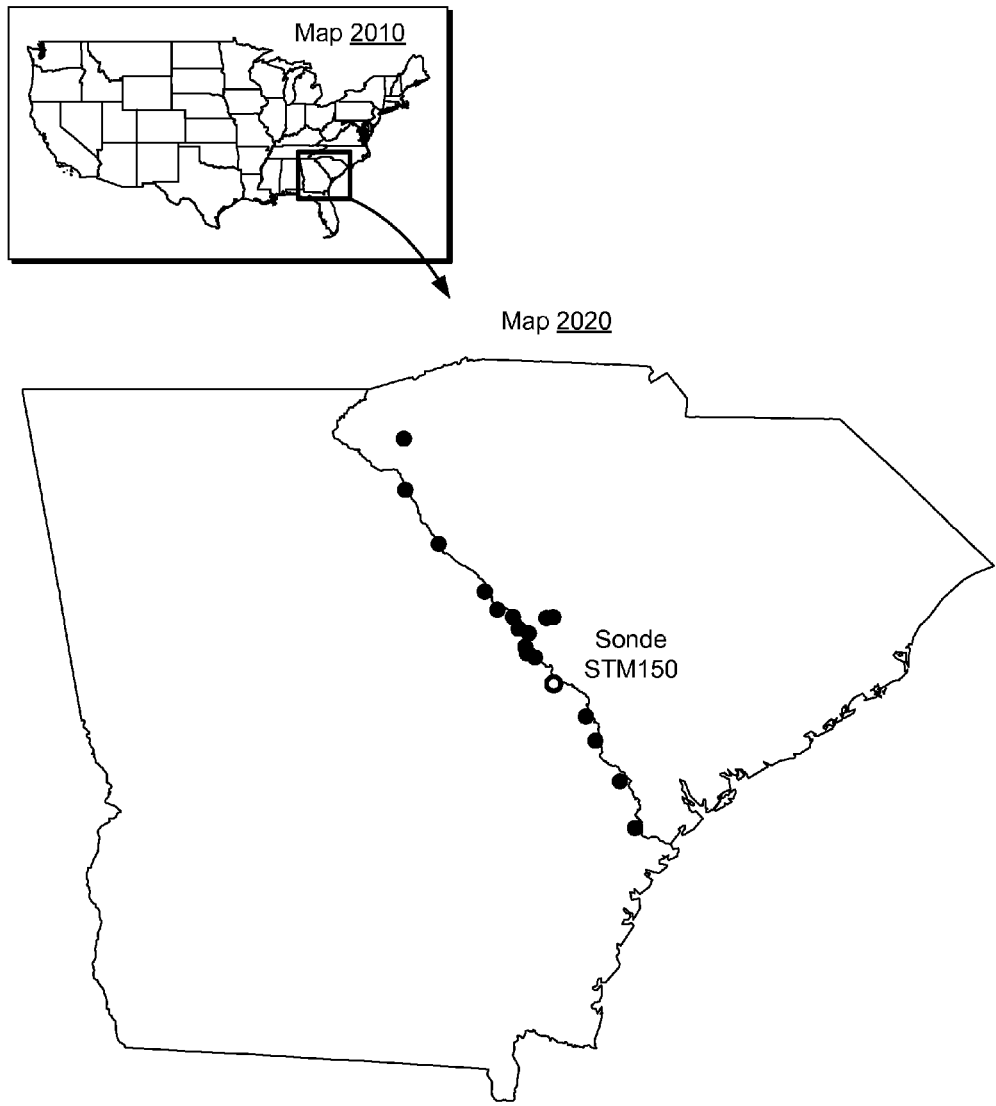
FIG. 20 is a diagram of an example of an environment that includes a plurality of sites.

FIG. 20 shows example maps 2010 and 2020 of an environment that includes a plurality of sites. The map 2020 shows the Savannah River as including tens of sites where each site can include one or more sondes. As an example, a graphical user interface (GUI) may render such a map and allow for interactions therewith.

As an example, information associated with a sonde may include information such as, for example, the information presented in Table 1 below.

TABLE 1

Example Sonde Information (e.g., multi-sensor sonde)

| Sensor Id | label | measures | units | latitude | longitude | altitude |
|---|---|---|---|---|---|---|
| 0-0 | Temp C. | Temperature | C. | 33.14036 | −81.74117 | undefined |
| 0-1 | spCond | Spec. Cond. | mS/cm | 33.14036 | −81.74117 | undefined |
| 0-2 | pH | pH | pH | 33.14036 | −81.74117 | undefined |
| 0-3 | Depth | Depth | meters | 33.14036 | −81.74117 | undefined |
| 0-4 | Turbidity NTU | Turbidity | fnu | 33.14036 | −81.74117 | undefined |
| 0-5 | ODO % sat | Dissol. O2 | % sat | 33.14036 | −81.74117 | undefined |
| 0-6 | ODO mg/L | Dissol. O2 | mg/L | 33.14036 | −81.74117 | undefined |
| 0-7 | Pwr V | Voltage | volts | 33.14036 | −81.74117 | undefined |

In Table 1, information is labeled as 0-0 to 0-7 and the location of the sonde is given in latitude and longitude, noting that altitude may optionally be defined. Such information may be accessible, for example, via communication circuitry (e.g., for wired and/or wireless communications) within a sonde and/or operatively coupled to a sonde. As an example, one or more of cellular, satellite, WI-FI™, BLUETOOTH™, ZIGBEE, etc., circuitry may be implemented. ZIGBEE is a specification for communication protocols that, for example, may be used to create networks via digital radio circuitry (e.g., consider an IEEE 802.15.4 standard, etc.).

As an example, devices may include circuitry to transmit data by passing data through a mesh network of intermediate devices to reach more distant ones. As an example, secure networking may be implemented (e.g., secured by multi-bit symmetric encryption keys, etc.). As an example, consider transmission at a rate of about several hundred kbit/s where such transmission may occur intermittently (e.g., according to a schedule, a trigger, etc.).

As an example, one or more sensors of a sonde may be associated with one or more types of contextual information. As an example, sensors of a sonde may be associated with manufacturer information (e.g., SKU, FRU, etc.), which can be a type of contextual information. Examples of contextual information can include, for example, types of configuration information (see, e.g., the configuration information 310 of FIG. 3). As an example, contextual information may be ascertained in the field, for example, via inspection of a sonde (e.g., whether by an operator, a remote tool, etc.). As an example, contextual information may be ascertained via one or more sources. For example, consider a fishing report with qualitative information that river flow was "high" for a particular period of time.

As an example, a sonde may be specified to operate for a number of days at a specified temperature with a specified logging interval and a specified sensor configuration (e.g., consider temperature/conductivity, pH/ORP, DO, total algae, and turbidity sensors). As an example, a sonde may include a wiper that operates at a particular rate such as, for example, a logging interval rate. As an example, where a sonde includes one or more batteries, battery life (e.g., number of days of operation, etc.) may depend on one or more factors (e.g., sensor configuration, logging interval, wiper rate, etc.). As an example, a code may indicate a number of days of operation remaining, for example, according to a predictive model, etc.

As an example, a sonde that includes multiple sensors powered by one or more batteries may experience an accelerated decline in power due to one or more conditions (e.g., one or more operational states of the sonde). Such a scenario may lead to uncertainty in one or more measurements taken by one or more sensors of the sonde. As an example, referring to the circuitry 820 of FIG. 8, where the voltage regulator 879 is unable to provide a sufficient voltage and/or sufficiently stable voltage, operation of one or more components associated with the TDS circuitry 866 may lead to uncertainty in measured TDS values. As an example, a system such as, for example, the system 300, may analyze received information (e.g., quantitative and/or qualitative) and determine whether such a scenario is due to the TDS sensing circuitry or circuitry associated with one or more other sensors. In such an example, measurements from the sonde may be tagged as to reliability, uncertainty, etc.

As an example, information may be output by a system that recommends maintenance of a sonde (e.g., replacement of one or more parts, one or more batteries, cleaning, greasing seals, etc.). Where reoccurrence of a scenario may be likely due to, for example, environmental conditions, a system may output a maintenance schedule, notifications, etc., that aim to increase measurement certainty, reliability, etc. In such an example, the output may include a cone of uncertainty as to maintenance given uncertainty in future environmental conditions. As an example, a system may output a "moving" cone of uncertainty that is adjusted over time as information about environmental conditions becomes known, more certain, etc.

As an example, a table such as, for example, Table 1, above, may include a column, etc., with an activatable link (e.g., a control) that may provide for accessing a system such as, for example, the system 300 of FIG. 3, to present information germane to operation of one or more of the sensors. Such information may, for example, include one or more of manufacturer information, maintenance information, histories of one or more other sensors that may share a common code (e.g., SKU, FRU, etc.), measurement uncertainty information (e.g., optionally condition-related, per temperature, length of operation, power level, etc.), power drain information (e.g., to schedule intervals to maintain a desired field life before battery replacement), etc. As an example, a table may include one or more types of contextual information, which may include quantitative and/or qualitative information.

As an example, a system such as, for example, the system 300 of FIG. 3, may receive information associated with one or more field installations and analyze such information to train one or more algorithms. For example, consider an artificial neural network that is trained based at least in part on information from the Savannah River locations illustrated in the map 2020 of FIG. 20. As an example, a network of artificial neural networks may be formulated, for example, where artificial neural networks may exist for individual sondes or groups of individual sondes and where an overarching artificial neural network exists for the Savannah River locations. In such an example, where a particular sonde is replaced (e.g., optionally with a differing sonde), a particular sub-network may be replaced for a system (e.g., a modular approach to an artificial neural network).

As an example, an artificial neural network may be trained using sonde data and optionally quantified qualitative data. For example, where qualitative data states, for example, seal O-rings lubricated due to indication of leakage, such a condition may be quantified as a condition upon which an artificial neural network may be trained. In such an example, where data are input to a trained artificial neural network, a probability may be determined as to the likelihood of occurrence of one or more conditions. Where a probability exceeds a threshold, a system may output information that maintenance, if performed within a period of time, may avoid a sonde experiencing a condition (e.g., a detrimental condition). While leakage is mentioned, it is an example, as conditions may include, for example, cleaning after a certain level of biofouling, battery replacement, sensor chemical(s) replacement, etc.

As to a biofouling condition, a system may include receiving information germane to a biological growth model of one or more organisms that can participate in biofouling that may impact operation of a sensor, reliability of sensed data, etc. In such an example, the system may include training one or more predictive models (e.g., neural network, etc.), receiving information, analyzing the information using at least one of the one or more predictive models and outputting information germane to operation and/or performance of a sonde (e.g., or sondes). As an example, a system may output a cleaning recommendation. In such an example, where cleaning is to be effectuated by visitation to a site of a sonde, the system may make one or more additional recommendations, for example, if power level is decreasing, an additional recommendation may be to replace one or more batteries (e.g., or check on circuitry that may be causing a drain in power, etc.).

Figure 21:
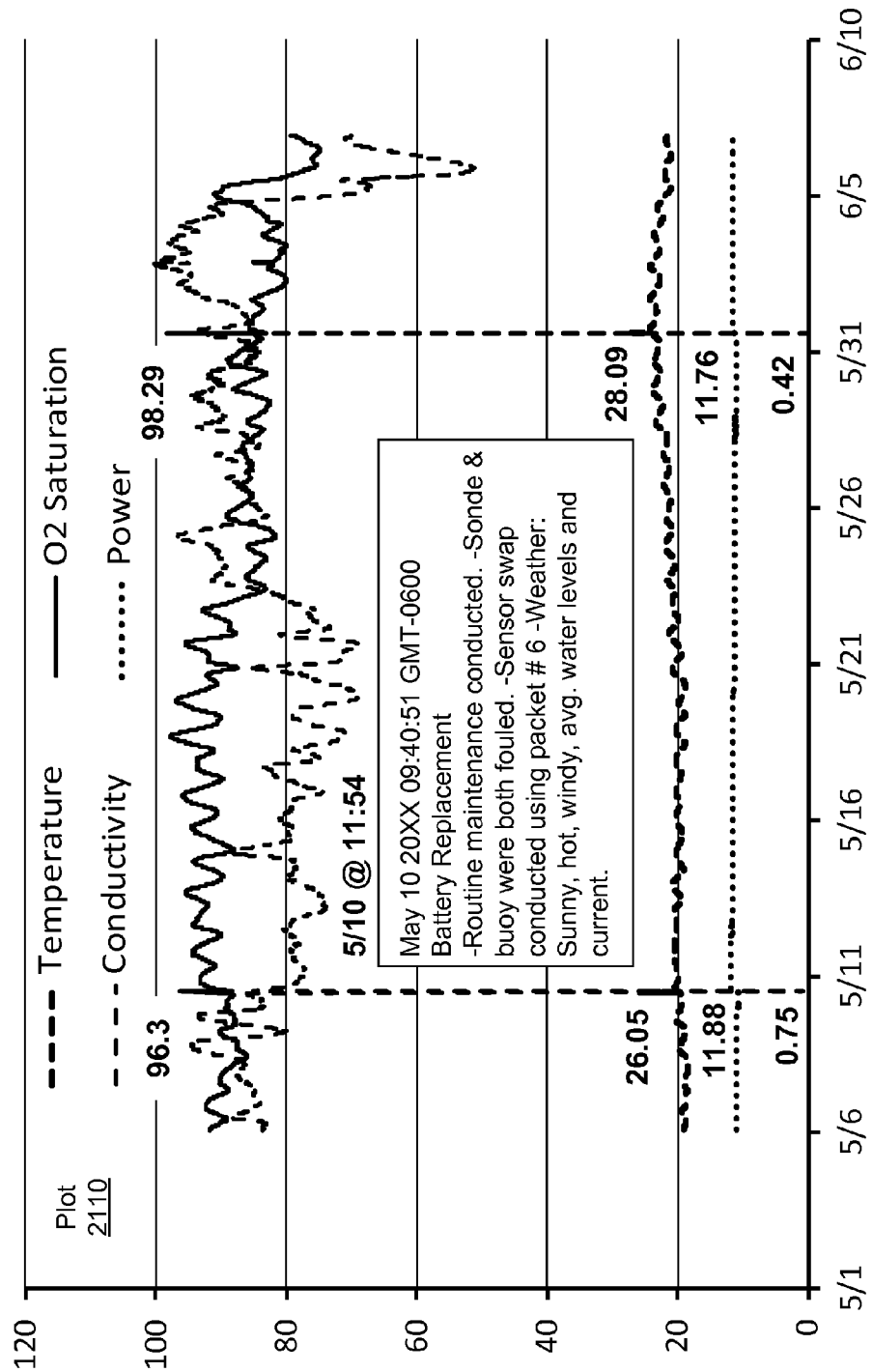
FIG. 21 is a diagram of an example of a plot of information.

FIG. 21 shows an example of a plot 2110 of information associated with a site identified as the STM150 sonde site in the map 2020 of FIG. 20. Specifically, the plot 2110 includes information as to temperature, conductivity, oxygen saturation and power over a span of about one month (see, e.g., sensors of Table 1).

The plot 2110 includes data that may be identified as being of questionable quality (e.g., uncertain, unreliable, etc.). For example, at about May 10, temperature values increase, power values increase, oxygen saturation values increase and conductivity values decrease. As an example, such information may be tagged for exclusion in a data analysis (e.g., by an operator of the sonde, etc.). For example, a system such as, for example, the system 300 of FIG. 3, may receiving information associated with the sonde that generated the data of the plot 2110 and analyze the information, optionally via one or more trained models to output information germane to data quality, operation of the sonde, performance of the sonde, maintenance of the sonde, etc. In such an example, the system may optionally associate measurements (e.g., measured values) with one or more codes that are indicative of one or more operational states of circuitry of the sonde (e.g., sensor circuitry, power circuitry, controller circuitry, memory circuitry, etc.).

In the example of FIG. 21, information may be available as to reasons why the values at about May 10 differ substantially from values before and after about May 10. For example, qualitative information may be available such as from maintenance personnel such as "Battery Replacement", "Routine maintenance conducted", "Sonde and buoy were both fouled", "Sensor swap conducted using packet #6", and "Weather: Sunny, hot, windy, avg. water levels and current".

Such qualitative information may be based on visual observations of equipment, weather, etc. directly by a maintenance person. As an example, a method may include transmitting information such as one or more of configuration information, measurement information and circuitry information, for example, as illustrated in FIG. 3. In such an example, a data analysis may be performed that aims to output results that may be germane to one or more conditions preceding the event or events at about May 10 in the plot 2110 of FIG. 21. As an example, one or more actions may be taken based at least in part on the output results, which may, for example, aim to address fouling of a sensor or sensors, etc. For example, consider ordering a replacement part and scheduling maintenance to install the replacement part, updating firmware (e.g., locally or remotely), rebooting circuitry (e.g., locally or remotely), etc. As an example, such one or more actions may include labeling (e.g., tagging with a code or codes) data, excluding data, etc. that may be compromised by one or more conditions, for example, as associated with the event or events at about May 10. By labeling (e.g., tagging with a code or codes) data, excluding data, etc., an operator of the sonde may increase its own data analysis and reporting capabilities.

Figure 22:
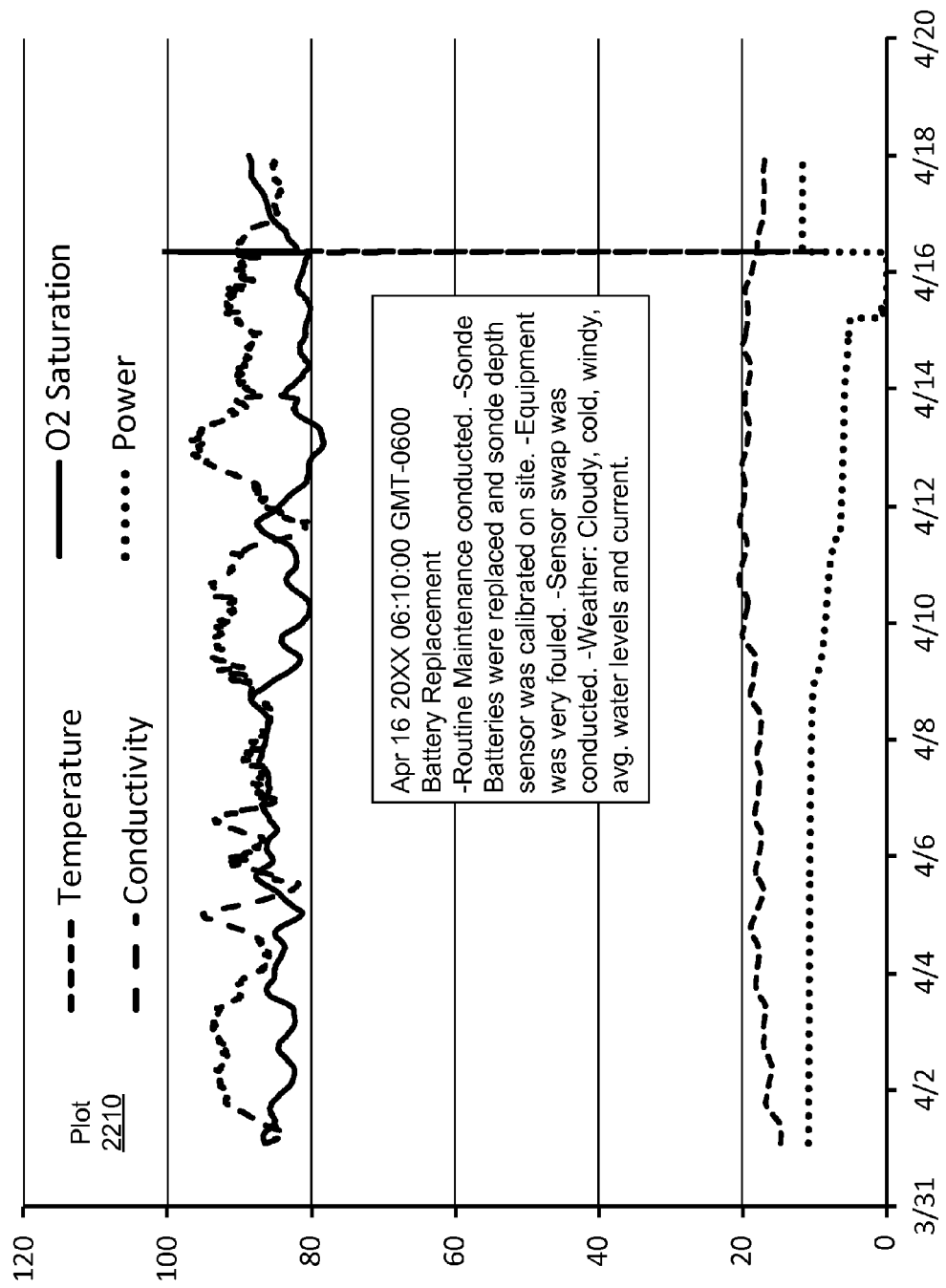
FIG. 22 is a diagram of an example of a plot of information.

FIG. 22 shows another example of a plot 2210 of information associated with a site identified as the STM150 sonde site in the map 2020 of FIG. 20. Specifically, the plot 2210 includes information as to temperature, conductivity, oxygen saturation and power over a span of less than about one month (see, e.g., sensors of Table 1).

In the example plot 2210, power decreases over time to a value of about zero at about April 15. In the example of FIG. 22, information may be available as to reasons why the values for power are decreasing. For example, qualitative information may be available such as from maintenance personnel such as "Battery Replacement", "Routine Maintenance conducted", "Sonde Batteries were replaced and sonde depth sensor was calibrated on site", "Equipment was very fouled", "Sensor swap was conducted", and "Weather: Cloudy, cold, windy, avg. water levels and current".

Such qualitative information may be based on visual observations of equipment, weather, etc. directly by a maintenance person. As an example, a method may include transmitting information such as one or more of configuration information, measurement information and circuitry information, for example, as illustrated in FIG. 3. In such an example, a data analysis may be performed that aims to output results that may be germane to one or more conditions preceding the event or events up to and including April 15 in the plot 2210 of FIG. 22. Such condition or conditions may include, for example, a circuitry associated where particular circuitry may be responsible for an undesirable level of power drain (e.g., due to malfunction, excessive sampling, load on a wiper due to heavy biofouling, etc.). As an example, one or more actions may be taken based at least in part on the output results, which may, for example, aim to address fouling of a sensor or sensors, etc. For example, consider ordering a replacement part and scheduling maintenance to install the replacement part, updating firmware (e.g., locally or remotely), rebooting circuitry (e.g., locally or remotely), etc. As an example, such one or more actions may include labeling (e.g., tagging with one or more codes) data, excluding data, etc. that may be compromised by one or more conditions, for example, as associated with the event or events leading up to and including April 15.

Figure 23:
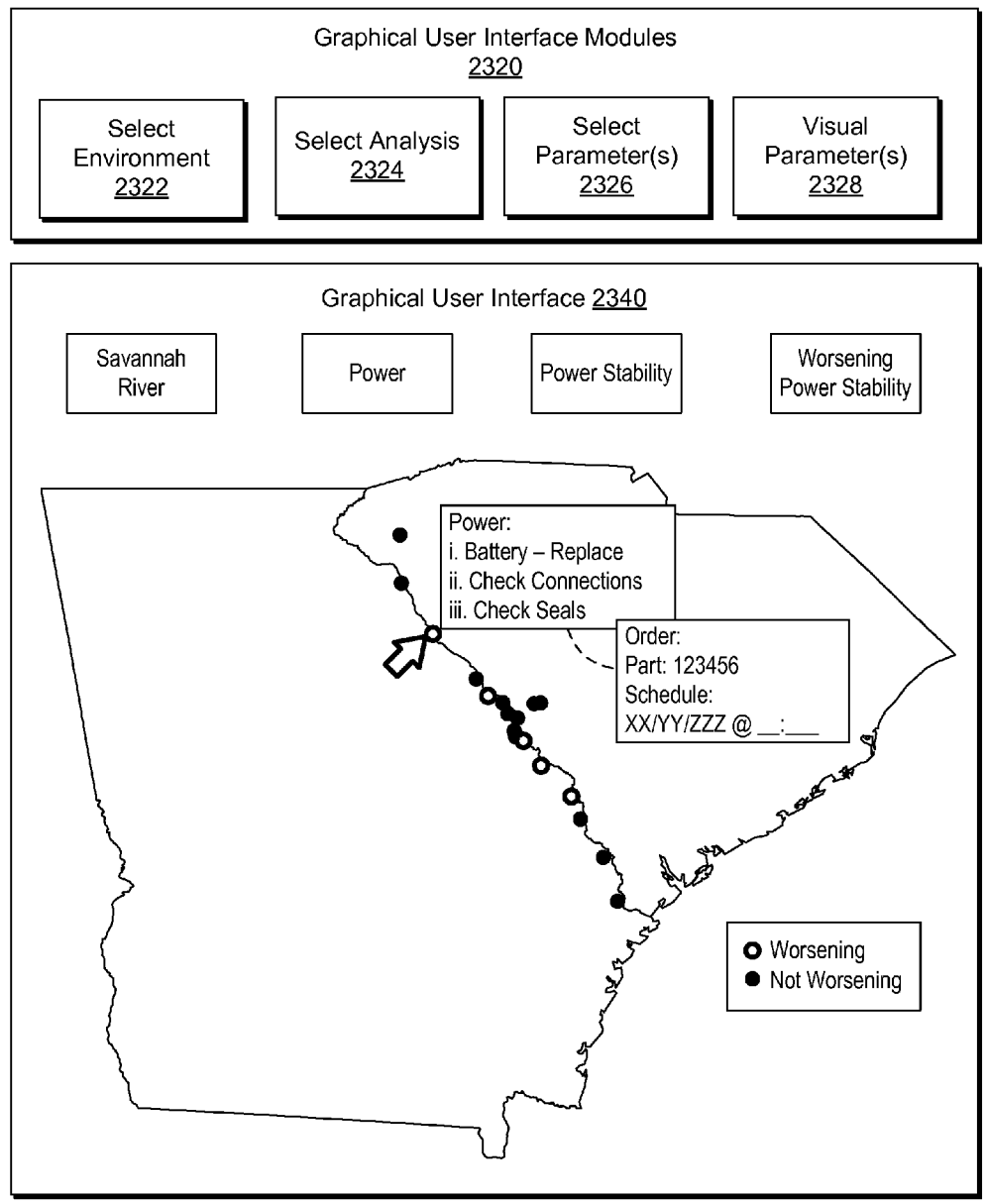
FIG. 23 is a diagram of examples of modules and an example of a graphical user interface.

FIG. 23 shows an example of modules 2320 and an example of a graphical user interface 2340. As shown, the modules 2320 can include a selection module 2322 to select an environment, a selection module 2324 to select an analysis, a selection module 2326 to select one or more parameters and a visualization module 2328 to visual one or more parameters (e.g., parameter values, etc.).

The GUI 2340 shows the Savannah River as a selected environment along with various sites. In the example of FIG. 23, a power analysis is selected and performed, for example, power stability may be determined via a power analysis (see, e.g., the plot 2210 of FIG. 22). As an example, the GUI 2340 may render visualizations that indicate which sites may be experiencing worsening power stability (see, e.g., the plot 2210 of FIG. 22) and, for example, other sites that may not be worsening (e.g., within appropriate limits).

As an example, the GUI 2340 may allow for interactions (e.g., via touch, mouse, voice command, stylus, etc.). As shown, a site may be selected to render additional information such as a maintenance regime to perform at the site based at least in part on worsening power stability at the site. For example, consider battery replacement, checking connections, checking biofouling and checking seals (e.g., as to leakage, etc.). As an example, a further interaction may allow for ordering of one or more parts and, for example, scheduling installation of such one or more parts (e.g., based on timings of availability, etc.).

Figure 24:
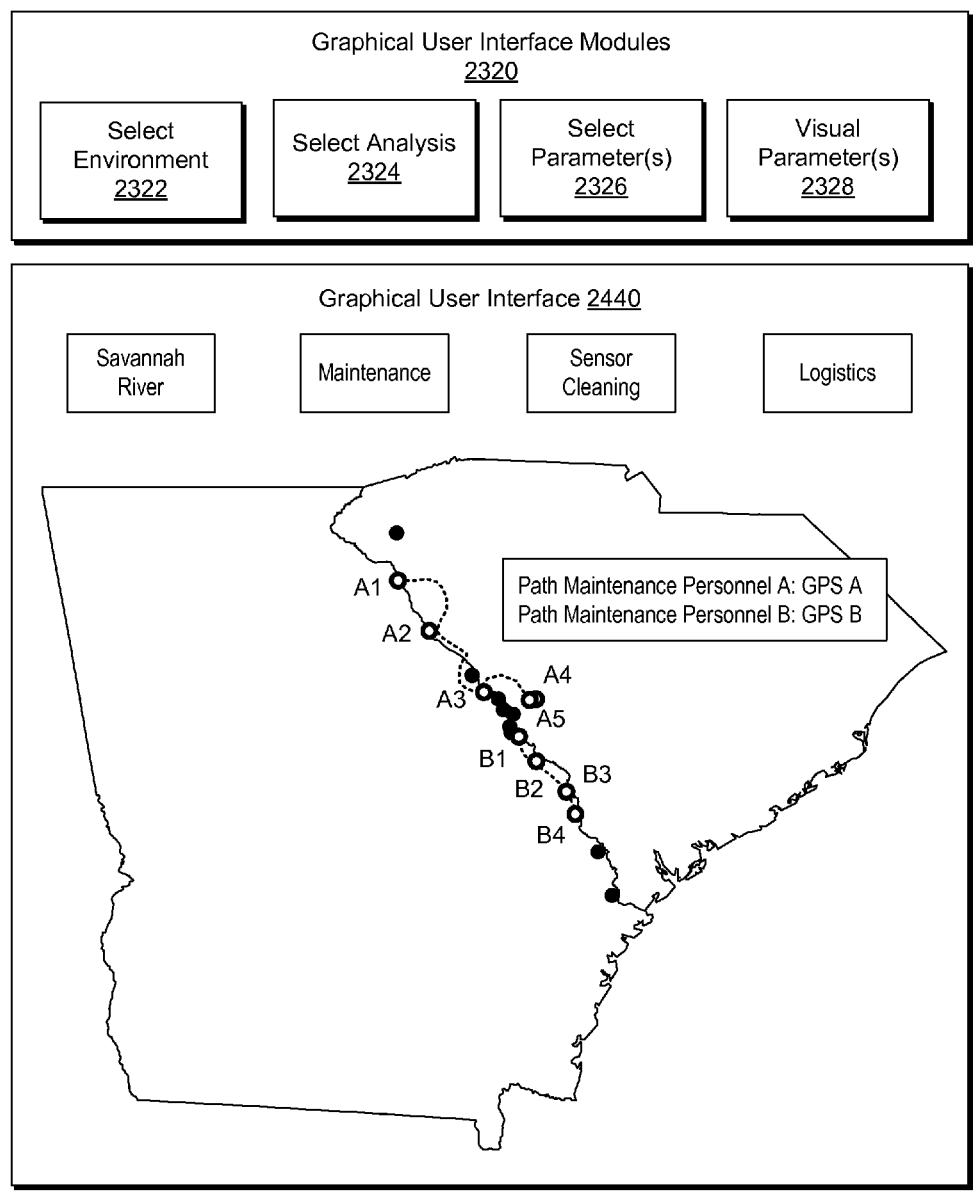
FIG. 24 is a diagram of examples of modules and an example of a graphical user interface.

FIG. 24 shows the example modules 2320 and an example of a graphical user interface 2440. In FIG. 24, the GUI 2440 shows the Savannah River as a selected environment along with various sites. In the example of FIG. 24, a maintenance analysis is selected and performed, for example, sensor cleanliness may be determined (e.g., degree of biofouling, etc.) via a maintenance analysis. As an example, the GUI 2440 may render visualizations that indicate which sites may be scheduled for sensor cleaning and, for example, with logistics as to paths for one or more maintenance personnel to travel to service the particular sites.

As an example, the GUI 2440 may allow for interactions (e.g., via touch, mouse, voice command, stylus, etc.). For example, a site may be selected to render additional information such as a maintenance regime to perform at the site based at least in part on a maintenance analysis for the site.

Figure 25:
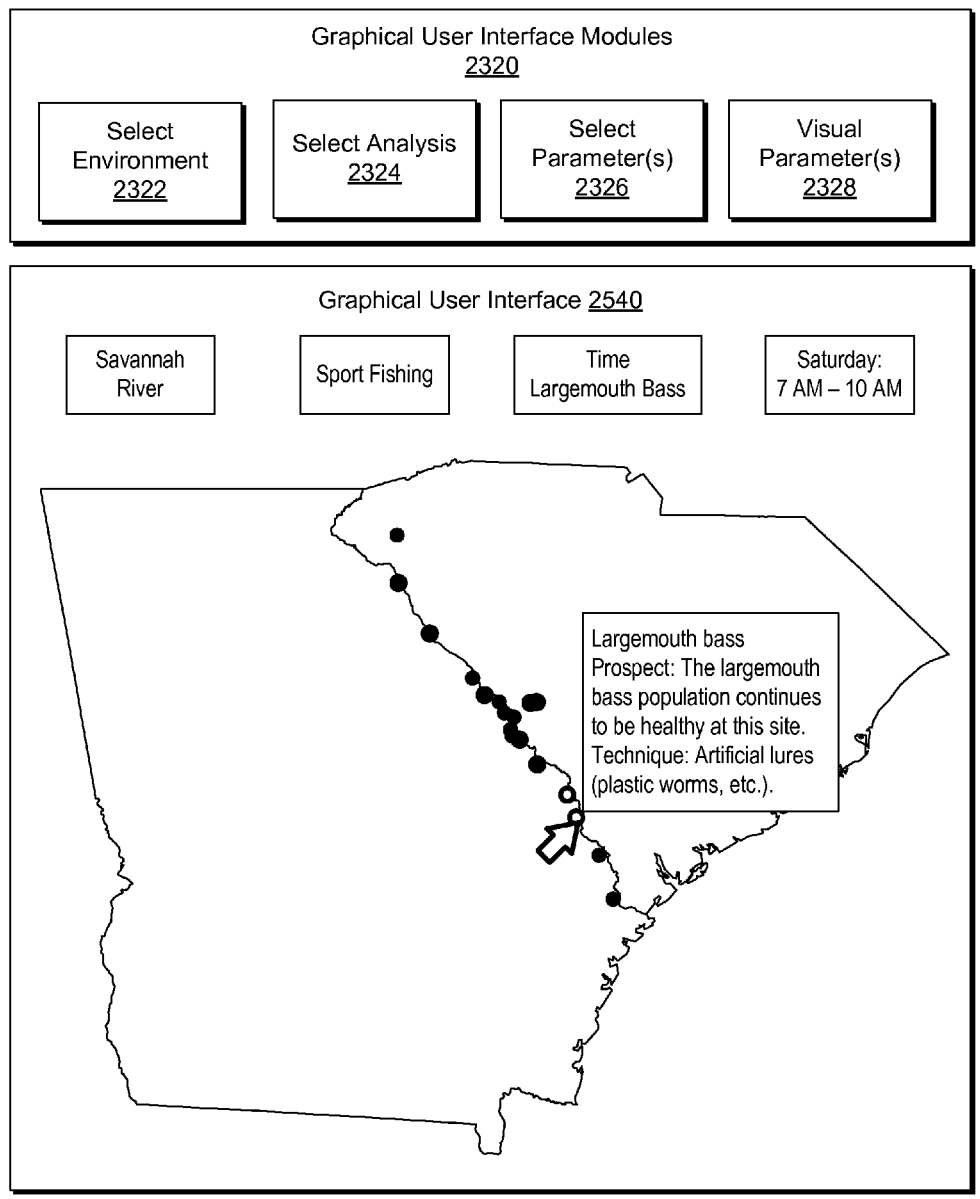
FIG. 25 is a diagram of examples of modules and an example of a graphical user interface.

FIG. 25 shows the example modules 2320 and an example of a graphical user interface 2540. In FIG. 25, the GUI 2540 shows the Savannah River as a selected environment along with various sites. In the example of FIG. 25, a sport fishing analysis is selected and performed, for example, times for fishing for largemouth bass may be determined via a sport fishing analysis. Such an analysis may be based at least in part on information from one or more sondes installed at one or more of the sites. As an example, the GUI 2540 may render visualizations that indicate which sites may be the best for sport fishing for largemouth bass, for example, within a time frame that one may have available for sport fishing. As an example, further interaction may access and render information such as, for example, prospect information (e.g., "largemouth bass population continues to be healthy at this site") and sport fishing information as to one or more techniques (e.g., "artificial lures (plastic worms, etc.)).

As an example, a GUI may be implemented via an "app", for example, consider a mobile phone based application (e.g., ANDROID™ OS, iOS™ OS, etc.). For example, a fisherman may instantiate an application (e.g., an "app") on a mobile phone where the application may render a GUI to a display of the mobile phone. In such an example, the mobile phone may receive input and, in turn, generate results (e.g., locally and/or remotely) and render information to the display such as information germane to fishing (see, e.g., the GUI 2540 of FIG. 25).

Figure 26:
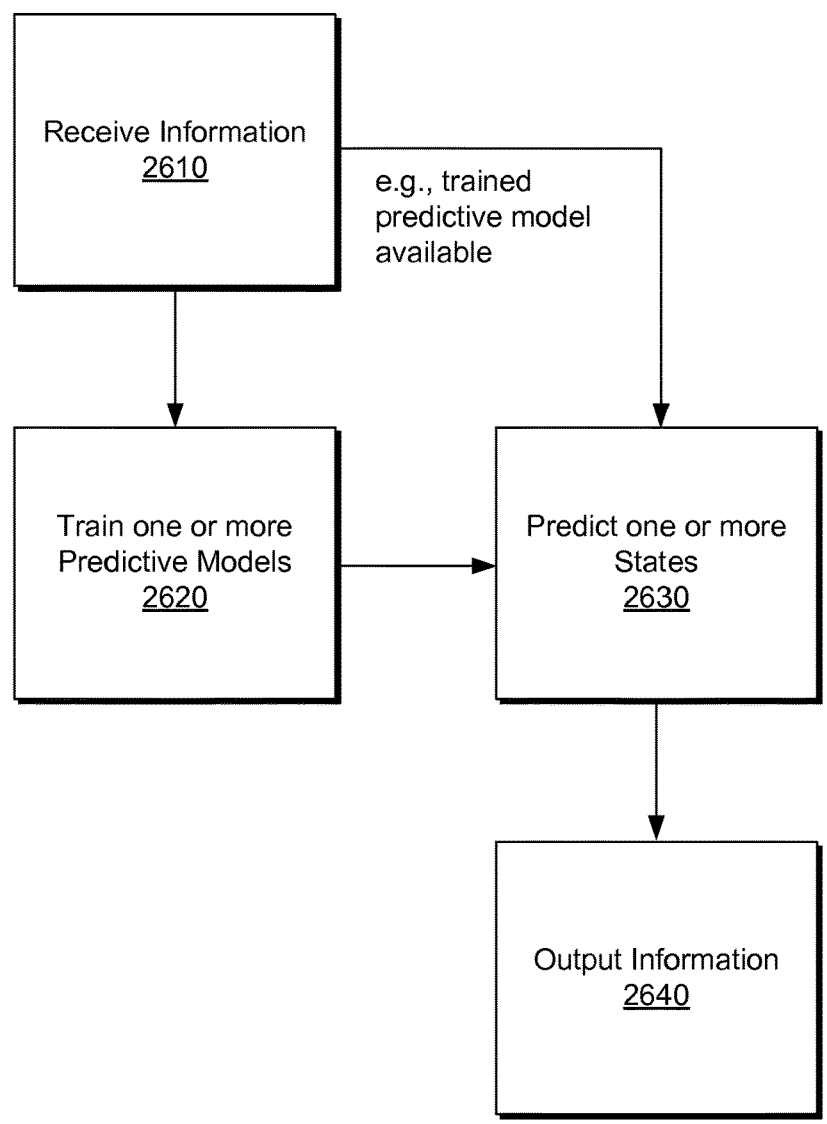
FIG. 26 is a diagram of an example of a method.

FIG. 26 shows an example of a method 2600 that includes a reception block 2610 for receiving information, a training block 2620 for training one or more predictive models based at least in part on a portion of the information, a prediction block 2630 for predicting one or more states via at least one trained predictive model and an output block 2640 for outputting information based at least in part on a prediction of at least one predictive model.

In the example of FIG. 26, the reception block 2610 may receive information from one or more remote sources. For example, consider receiving information via the Internet as to installations of a plurality of sondes (e.g., consider an application programming interface (API) that may allow for accessing information from one or more databases via a network). In such an example, qualitative information may be available together with measurement information and, for example, manufacturer information as to types of sondes, sensors, etc. As an example, such information may be utilized to train one or more predictive models. For example, consider the information of the plot 2210 of FIG. 22. In such an example, measurement information may be used to train a predictive model as to an outcome state (e.g., an operational state) that indicates worsening power stability (e.g., via quantitative and/or qualitative information), which may, for example, call for one or more remedial actions (e.g., inspection, battery replacement, servicing, etc.). In such an example, the trained predictive model may be utilized to analyze information received pertaining to one or more other sondes (e.g., based on one or more of installation site, environmental conditions, manufacturer, etc.). The trained predictive model may output information, for example, to notify an operator, manufacturer, etc., that an operational state exists or has a probability of existing for one or more sondes. In turn, remedial action may be recommended to address the operational state, which may be represented by a code and, for example, an associated textual description. As an example, measurement values for one or more sensors of a sonde may be tagged with a code, which may indicate that the measurement values should be, for example, excluded from an assessment of an environment (e.g., due to the particular operational state of a sensor, sensors, a sonde, etc.). As explained, output information may include information germane to measured values (e.g., quality, etc.) and information germane to operation of equipment (e.g., one or more sensors, sondes, etc.). Such output information may prove to enhance data integrity and integrity of assessments that rely on such data.

As an example, an environment may include a plurality of sondes, which may be located on land, on water, etc. As an example, an analysis may indicate that a density of sondes is to be increased, for example, to account for one or more conditions (e.g., a new factory, a new source of emissions, etc.). As an example, an analysis may include recommending that one or more sondes be relocated and/or that one or more new sondes be installed in an environment. As an example, a relocation recommendation may be based on one or more conditions such as electromagnetic interference, etc.

As an example, an analysis may be performed that outputs information germane to sampling rates (e.g., measurement frequency). For example, where a variable is found to be substantially constant with respect to time, a frequency may be decreased, which, in turn, may conserve power and/or one or more other resources of a sonde (e.g., or maintenance personnel, data storage, etc.).

As an example, a system may receive information for different types of sensors, sondes, etc. As an example, a system may transmit information to a manufacturer of a sensor, a sonde, etc., for example, particularly as to quality of measurement, performance, replacement, firmware upgrade, etc.

As an example, a system may be configured to handle and analyze information associated with water quality measurement devices such as a sonde that can measure at least temperature, conductivity, pH and dissolved oxygen (e.g., also consider turbidity). As an example, an analysis may include inputting information to one or more artificial neural networks and outputting information based at least in part on the analysis. Such information may include, for example, information germane to underlying relationships, for example, temperature and DO may be analyzed as to their correlation.

As an example, a system may output information as to a water quality index, which may, for example, be based on a plurality of different types of measurements. In such an example, consider a water quality index that is based on four underlying measurement types. Where an analysis indicates that quality of one or more of the underlying measurement types may be compromised (see, e.g., the plots 2120 and 2220), the water quality index may be presented, stored, etc., with an indicator as to its uncertainty (e.g., "water quality index with uncertain pH").

As an example, an analysis may consider one or more biological processes. For example, consider algae blooms that may generate oxygen and then die and consume oxygen, which may thereby alter DO levels in water. Such information may be associated with one or more models such as, for example, a photosynthesis model, a weather model, a night/day model, etc. As an example, information as to one or more biological cycles may be used in predicting performance, lifespan, etc., of one or more components of a sonde. For example, where conditions exist for biological growth that may foul one or more sensors of a sonde, such conditions may be taken into account in analyzing and predicting performance of a sonde, maintenance of a sonde, etc.

As an example, a system may include an ecosystem model. As an example, such a model may model relationships between water, insects and fish. As an example, a system may include a model as to quality of water for purposes of one or more of swimming, fishing and drinking. As an example, an ecosystem model may model discharge from one or more facilities such as, for example, a wastewater treatment facility. In such an example, a system may output information as to one or more of swimming, fishing and drinking for a population that may be located in a region impacted by such discharge (e.g., a population that can interact with the ecosystem).

As an example, an apparatus can include a controller; memory accessible to the controller; a bus operatively coupled to the controller; sensor circuitry operatively coupled to the bus where the sensor circuitry generates measurement information representative of an environmental condition; and where the controller determines codes, each of the codes representative of an individual operational state of the apparatus, and wherein the controller associates, in the memory, at least a portion of the measurement information with at least one of the codes. In such an example, the codes can include codes derived from an analysis of historical individual operational states. As an example, codes may include one or more of a bus error code, a calibration error of sensor circuitry code, a controller instruction error code, an analog-to-digital conversion error code, a memory error code, a reset error code, a clock error or one or more other types of codes.

As an example, a method can include receiving information associated with operational states of a plurality of apparatuses where each of the apparatuses includes a controller, memory accessible to the controller, a bus operatively coupled to the controller, and sensor circuitry operatively coupled to the bus where the sensor circuitry generates measurement information representative of an environmental condition; generating a model based at least in part on the information; and deriving codes based at least in part on the model where each of the codes corresponds to an apparatus-detectable individual operational state. In such an example, the method can include training an artificial neural network to generate a trained artificial neural network model.

As an example, a method can include receiving information that includes sets of configuration information corresponding to individual apparatuses where each of the sets of configuration information can include configuration information generated by the individual apparatuses and configuration information input to the individual apparatuses. As an example, information may include sets of circuitry information corresponding to individual apparatuses where such sets of circuitry information can include static information and/or dynamic information (e.g., for circuitry of an apparatus).

As an example, a method can include receiving measurement information and associated codes from an apparatus that includes a controller that includes memory accessible to the controller, a bus operatively coupled to the controller, sensor circuitry operatively coupled to the bus where the sensor circuitry generates measurement information representative of an environmental condition, where the controller determines the codes, each of the codes representative of an individual operational state of the apparatus; analyzing the received measurement information and associated codes; and transmitting at least one instruction to the apparatus based at least in part on the analyzing. In such an example, analyzing can include inputting at least a portion of the received codes into a predictive model. As an example, consider predicting a mode of failure of an apparatus via a predictive model and transmitting at least one instruction as a corrective instruction intended to avoid the predicted mode of failure of the apparatus.

As an example, a server can include a processor; memory accessible to the processor; a network interface; and processor-executable instructions stored in the memory and executable by the processor to instruct the server to perform operations including: receiving measurement information and associated codes from an apparatus via the network interface; analyzing the received measurement information and associated codes; and transmitting via the network interface information based at least in part on the analyzing. In such an example, the transmitting can transmit at least one instruction to the apparatus based at least in part on the analyzing and/or can transmit at least one alert based at least in part on the analyzing (e.g., consider an alert associated with an operational condition of the apparatus).

A system can include a processor; memory accessible to the processor; a network interface; and processor-executable instructions stored in the memory and executable by the processor to instruct the system to where the instructions include instructions to: receive measurement information and at least one associated code from an apparatus via the network interface; perform an analysis of the received measurement information and the at least one associated code; and transmit via the network interface information based at least in part on the analysis of the received measurement information and the at least one associated code. In such an example, the instructions to transmit can include instructions to transmit at least one instruction to the apparatus based at least in part on the analysis.

As an example, a system can include instructions to transmit at least one alert based at least in part on an analysis where the at least one alert includes an alert associated with an operational condition of the apparatus.

As an example, a system can include a server that includes a processor, memory accessible to the processor, and a network interface; and a sonde that includes a controller, memory accessible to the controller, a bus operatively coupled to the controller, a communication interface, and sensor circuitry operatively coupled to the bus where the sensor circuitry generates measurement information, where the controller determines codes, each of the codes representative of an individual operational state of the sonde, where the controller associates, in the memory of the sonde, at least a portion of the measurement information with at least one of the codes, and where the communication interface transmits the at least a portion of the measurement information and the at least one associated code to the server (e.g., for receipt by the server via the network interface).

As an example, a system can include a sonde that includes a controller, memory accessible to the controller, a bus operatively coupled to the controller, a communication interface, and sensor circuitry operatively coupled to the bus where the sensor circuitry generates measurement information representative of an environmental condition, where the controller determines codes, each of the codes representative of an individual operational state of the sonde, and where the controller associates, in the memory, at least a portion of the measurement information with at least one of the codes; and a server that includes a processor, memory accessible to the processor, a communication interface and processor-executable instructions stored in the memory and executable by the processor to instruct the server to perform operations including receiving measurement information and associated codes from the sonde via the communication interfaces, analyzing the received measurement information and associated codes and transmitting via the communication interface of the server information (e.g., alerts, instructions, etc.) based at least in part on the analyzing.

Although various examples of methods, devices, systems, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, etc.

What is claimed is:

1. An apparatus comprising:
   a controller;
   memory accessible to the controller;
   a bus operatively coupled to the controller;
   sensor circuitry operatively coupled to the bus wherein the sensor circuitry generates measurement information representative of an environmental condition of an environment of the apparatus and related to an attribute of water and wherein contextual information is determined from the environmental condition;
   wherein the controller determines codes, each of the codes representative of an individual operational state of the apparatus, the individual operational state being determined from the contextual information and indicates an operational status of a component of the apparatus, and wherein each of the codes is determined based upon the controller associating, in the memory, the operational status of a component as determined using at least a portion of the measurement information with at least one of the codes wherein, based upon the at least one of the codes, the controller determines an acceptability of the measurement information for inclusion in determining the environmental condition of the environment of the apparatus.

2. The apparatus of claim 1 wherein the codes comprise codes derived from an analysis of historical individual operational states.

3. The apparatus of claim 1 wherein at least one of the codes corresponds to an individual operational state that comprises a bus error.

4. The apparatus of claim 1 wherein at least one of the codes corresponds to an individual operational state that comprises a calibration error of the sensor circuitry.

5. The apparatus of claim 1 wherein at least one of the codes corresponds to an individual operational state that comprises a controller instruction error.

6. The apparatus of claim 1 wherein at least one of the codes corresponds to an individual operational state that comprises an analog-to-digital conversion error.

7. The apparatus of claim 1 wherein at least one of the codes corresponds to an individual operational state that comprises a memory error.

8. The apparatus of claim 1 wherein at least one of the codes corresponds to an individual operational state that comprises a reset error.

9. The apparatus of claim 1 wherein at least one of the codes corresponds to an individual operational state that comprises a clock error.

10. The apparatus of claim 1 wherein the sensor circuitry comprises oxygen sensor circuitry.

11. The apparatus of claim 1 wherein the sensor circuitry comprises dissolved solids sensor circuitry.

12. A method comprising:
receiving information associated with operational states of a plurality of apparatuses wherein each of the apparatuses comprise a controller, memory accessible to the controller, a bus operatively coupled to the controller, and sensor circuitry operatively coupled to the bus wherein the sensor circuitry generates measurement information representative of an environmental condition of an environment of each of the apparatuses and related to an attribute of water and wherein contextual information is determined from the environmental condition;
generating a model based at least in part on the information;
deriving codes based at least in part on the model wherein each of the codes corresponds to an apparatus-detectable individual operational state, the individual operational state being determined from the contextual information and indicates an operational status of a component of the apparatus and wherein each of the codes is derived based upon associating the operational status of a component as determined using at least a portion of the measurement information with at least one of the codes wherein, based upon the at least one of the codes, determining an acceptability of the measurement information for inclusion in determining the environmental condition of the environment; and
transmitting controller instructions to one of the apparatuses wherein the instructions, responsive to detection of an apparatus-detectable individual operational state by the one of the apparatuses, instruct its controller to store a corresponding one of the codes to its memory.

13. The method of claim 12 wherein the generating a model comprises training an artificial neural network to generate a trained artificial neural network model.

14. The method of claim 12 wherein the information comprises sets of configuration information corresponding to the individual apparatuses wherein each of the sets of configuration information comprises configuration information generated by the individual apparatuses and configuration information input to the individual apparatuses.

15. The method of claim 12 wherein the information comprises sets of circuitry information corresponding to the individual apparatuses wherein the sets of circuitry information comprise static information and dynamic information.

16. A method comprising:
receiving measurement information and associated codes from an apparatus that comprises a controller that comprises memory accessible to the controller, a bus operatively coupled to the controller, sensor circuitry operatively coupled to the bus wherein the sensor circuitry generates measurement information representative of an environmental condition of an environment of the apparatus and related to an attribute of water and wherein contextual information is determined from the environmental condition, wherein the controller determines the codes, each of the codes representative of an individual operational state of the apparatus, the individual operational state being determined from the contextual information and indicates an operational status of a component of the apparatus and wherein each of the codes is determined based upon associating the operational status of a component as determined using at least a portion of the measurement information with at least one of the codes;
analyzing the received measurement information and associated codes wherein the analyzing comprises inputting at least a portion of the received codes into a predictive model, wherein the analyzing comprises, based upon the at least one of the codes, determining an acceptability of the measurement information for inclusion in determining the environmental condition of the environment;
predicting a mode of failure of the apparatus via the predictive model and based upon the associated codes; and
transmitting at least one instruction to the apparatus based at least in part on the analyzing wherein the at least one instruction comprises a corrective instruction intended to avoid the predicted mode of failure of the apparatus.

17. A system comprising:
a processor;
memory accessible to the processor;
a network interface; and
processor-executable instructions stored in the memory and executable by the processor to instruct the system wherein the instructions comprises instructions to:
receive measurement information representative of an environmental condition of an environment of the apparatus and related to an attribute of water and wherein contextual information is determined from the environmental condition and at least one associated code from an apparatus via the network interface wherein the at least one code comprises a code representative of an individual operational state of the apparatus, the individual operational state being determined from the contextual information and indicates an operational status of a component of the apparatus and wherein the at least one associated code is determined based upon associating the operational status of a component as determined using at least a portion of the measurement information with at least one of code;
perform an analysis of the received measurement information and the at least one code wherein the analysis performs an assessment of at least a portion of the measurement information with respect to the code representative of an individual operational state of the apparatus, wherein the analysis determines an acceptability of the measurement information for inclusion in determining the environmental condition of the environment; and
transmit via the network interface information based at least in part on the analysis of the received measurement information and the at least one code.

18. The system of claim 17 wherein the instructions to transmit comprise instructions to transmit at least one instruction to the apparatus based at least in part on the analysis.

19. The system of claim 17 wherein the instructions to transmit comprise instructions to transmit at least one alert based at least in part on the analysis wherein the at least one alert comprises an alert associated with an operational condition of the apparatus.

20. The system of claim 17 comprising
a server that comprises the processor, the memory accessible to the processor, and the network interface; and
the apparatus wherein the apparatus comprises a sonde that comprises a controller, memory accessible to the controller, a bus operatively coupled to the controller, a communication interface, and the sensor circuitry operatively coupled to the bus wherein the sensor circuitry generates measurement information, wherein the controller determines codes, each of the codes representative of an individual operational state of the sonde, wherein the controller associates, in the memory of the sonde, at least a portion of the measurement information with at least one of the codes, and wherein the communication interface transmits the at least a portion of the measurement information and the at least one associated code to the server.

* * * * *